US012692542B2

(12) United States Patent
Cheishvili et al.

(10) Patent No.: US 12,692,542 B2
(45) Date of Patent: Jul. 28, 2026

(54) EPIAGING ; NOVEL ECOSYSTEM FOR MANAGING HEALTHY AGING

(71) Applicant: HKG EPITHERAPEUTICS LIMITED, Pierrefonds (CA)

(72) Inventors: David Cheishvili, Pierrefonds (CA); Moshe Szyf, Cote St Luc (CA); Chi Fat Wong, Hong Kong (CN); Hui Li, Hong Kong (HK)

(73) Assignee: EpiMedTechGlobal (EMTG), Singapore (SG)

( * ) Notice: Subject to any disclaimer, the term of this patent is extended or adjusted under 35 U.S.C. 154(b) by 1013 days.

(21) Appl. No.: 17/614,178

(22) PCT Filed: May 29, 2020

(86) PCT No.: PCT/IB2020/055146
§ 371 (c)(1),
(2) Date: Nov. 24, 2021

(87) PCT Pub. No.: WO2020/240511
PCT Pub. Date: Dec. 3, 2020

(65) Prior Publication Data
US 2022/0228217 A1     Jul. 21, 2022

Related U.S. Application Data

(60) Provisional application No. 62/854,226, filed on May 29, 2019.

(51) Int. Cl.
*C12Q 1/6883* (2018.01)
*G16B 20/20* (2019.01)
*G16B 40/20* (2019.01)

(52) U.S. Cl.
CPC ........... *C12Q 1/6883* (2013.01); *G16B 20/20* (2019.02); *G16B 40/20* (2019.02); *C12Q 2600/154* (2013.01); *C12Q 2600/16* (2013.01)

(58) Field of Classification Search
CPC ........... C12Q 1/6883; C12Q 2600/154; C12Q 2600/16; G16B 20/20; G16B 20/00; G16B 40/20; G16B 40/00
See application file for complete search history.

(56) References Cited

U.S. PATENT DOCUMENTS

| | | | | |
|---|---|---|---|---|
| 2002/0119503 A1* | 8/2002 | Ryan | ......................... | G01N 1/30 |
| | | | | 435/288.5 |
| 2006/0196785 A1* | 9/2006 | Lanier | .................... | A61C 19/00 |
| | | | | 206/223 |
| 2013/0323220 A1* | 12/2013 | Joung | ..................... | A61P 35/00 |
| | | | | 435/375 |
| 2017/0290516 A1 | 10/2017 | Nguyen et al. | | |
| 2017/0342496 A1* | 11/2017 | Zhang | .................. | C12Q 1/6883 |
| 2020/0190568 A1* | 6/2020 | Boroni Martins | ..... | G06N 20/10 |

FOREIGN PATENT DOCUMENTS

| | | |
|---|---|---|
| EP | 3070626 | 9/2016 |
| JP | 2009535050 A | 10/2009 |
| JP | 2011-505812 | 3/2011 |
| JP | 2011505812 A | 3/2011 |
| JP | 2017-86043 | 5/2017 |
| JP | 2017086043 | 5/2017 |
| KR | 20170015456 | 2/2017 |
| WO | 2017048673 | 3/2017 |
| WO | WO2018/229032 | 12/2018 |

OTHER PUBLICATIONS

Chihiro Iwaya, "Comparative study of age-associated epigenetic modifications using human cohorts and mouse models," Thesis, pp. 1-83. (Year: 2018).*
GenBank Accession AL121955.20. (Year: 2012).*
Bacalini et al., "Systemic Age-Associated DNA Hypermethylation of ELOVL2 Gene: In Vivo and In Vitro Evidences of a Cell Replication Process," Journal of Gerontology: Biological Sciences, vol. 72, No. 8, pp. 1015-1023. (Year: 2017).*
Gene Expression Online, Series GSE40279. (Year: 2012).*
Hamano et al., "Forensic age prediction for dead or living samples by use of methylation-sensitive high resolution melting," Legal Medicine, vol. 21, pp. 5-10. (Year: 2016).*
Rönn et al., "Impact of age, BMI and HbA1c levels on the genomewide DNA methylation and mRNA expression patterns in human adipose tissue and identification of epigenetic biomarkers in blood," Human Molecular Genetics, vol. 24, No. 13, pp. 3792-3813. (Year: 2015).*
Zbieć-Piekarska et al., "Development of a forensically useful age prediction method based on DNA methylation analysis," Forensic Science International: Genetics, vol. 15, pp. 173-179. (Year: 2015).*
Renata Zbiec-Piekarska et al: "Examination of DNA methylation status of the ELOVL2 marker may be useful for human age prediction in forensic science", Forensic Science International: Genetics, vol. 14, Dec. 31, 2015 (Dec. 31, 2015), pp. 161-167, XP055757275.

(Continued)

*Primary Examiner* — Samuel C Woolwine
*Assistant Examiner* — Francesca Filippa Giammona

(57)     ABSTRACT

The present invention relates to method for calculating biological age of a subject and across multiple subjects by performing polygenic DNA methylation on biomarkers which comprise measuring the methylation status of 13 CG sites positioned in a putative antisense region to ElovL2 gene, ElovL2 AS1 region. Further, the present invention provides a computer-implemented method for providing recommendations for lifestyle changes in form of a self-learning "ecosystem" for lifestyle management of biological aging using a novel measurement of the DNA methylation clock as a continuous dynamic outcome. The present invention also relates to combination of DNA methylation biomarkers for calculating biological age, a kit for determining the biological age. Further, the present invention discloses the use of the disclosed methods for calculating biological age in a method of assessing the effect of the effect of a biological intervention and in a method of screening for an anti-ageing agent.

6 Claims, 4 Drawing Sheets

Specification includes a Sequence Listing.

(56) References Cited

OTHER PUBLICATIONS

Sang-Eun Jung et al: "DNA methylation of the ELOVL2, FHL2, KLF14, 1orf132/MIR2982C, and TRIM59 genes for age prediction from blood, saliva, and buccal swab samples", Forensic Science International: Genetics, vol. 38, Sep. 29, 2018 (Sep. 29, 2018), pp. 1-8, XP055757307.

Spòlnicka M et al: "DNA methylation in ELOVL2 and C1orf132 correctly predicted chronological age of individuals from three disease groups", International Journal of Legal Medicine, Springer Berlin Heidelberg, Berlin/Heidelberg, vol. 132, No. 1, Jul. 19, 2017 (Jul. 19, 2017), pp. 1-11, XP037216029.

Paolo Garagnani et al: "Methylation of ELOVL 2 gene as a new epigenetic marker of age", Aging Cell, vol. 11, No. 6, Oct. 14, 2012 (Oct. 14, 2012), pp. 1132-1134, XP055069767.

European Search Report; 20814552.4; Dec. 17, 2022; Barz Wolfgang.

Beauchaine, T. P., & Beauchaine, R. J., 3rd. (2002). A comparison of maximum covariance and K-means cluster analysis in classifying cases into known taxon groups. Psychol Methods, 7(2), 245-261.

Bybee, S. M., Bracken-Grissom, H., Haynes, B. D., Hermansen, R. A., Byers, R. L., Clement, M. J., . . . Crandall, K. A. (2011). Targeted amplicon sequencing (TAS): a scalable next-gen approach to multilocus, multitaxa phylogenetics. Genome Biol Evol, 3, 1312-1323. doi:10.1093/gbe/evr106.

Chen, B. H., Marioni, R. E., Colicino, E., Peters, M. J., Ward-Caviness, C. K., Tsai, P. C., . . . Horvath, S. (2016). DNA methylation-based measures of biological age: meta-analysis predicting time to death. Aging (Albany NY), 8(9), 1844-1865. doi:10.18632/aging.101020.

Colella, S., Shen, L., Baggerly, K. A., Issa, J. P., & Krahe, R. (2003). Sensitive andquantitative universal Pyrosequencing methylation analysis of CpG sites. Biotechniques, 35(1), 146-150.

De Roach, J. N. (1989). Neural networks—an artificial intelligence approach to the analysis of clinical data. Australas Phys Eng Sci Med, 12(2), 100-106.

Ferrucci, L., Cavazzini, C., Corsi, A., Bartali, B., Russo, C. R., Lauretani, F., . . . Guralnik, J. M. (2002). Biomarkers of frailty in older persons. J Endocrinol Invest, 25(10 Suppl), 10-15.

Freire-Aradas, A., Phillips, C., Mosquera-Miguel, A., Giron-Santamaria, L., Gomez-Tato, A., Casares de Cal, M., . . . Lareu, M. V. (2016). Development of a methylation marker set for forensic age estimation using analysis of public methylation data and the Agena Bioscience EpiTYPER system. Forensic Sci Int Genet, 24, 65-74. doi:10.1016/j.fsigen.2016.06.005.

Hardy, A., & Magnello, M. E. (2002). Statistical methods in epidemiology: Karl Pearson, Ronald Ross, Major Greenwood and Austin Bradford Hill, 1900-1945. Soz Praventivmed, 47(2), 80-89.

Hertel, J., Friedrich, N., Wittfeld, K., Pietzner, M., Budde, K., Van der Auwera, S., . . . Grabe, H. J. (2016). Measuring Biological Age via Metabonomics: The Metabolic Age Score. J Proteome Res, 15(2), 400-410. doi:10.1021/acs.jproteome.5b00561.

Horvath, S. (2013). DNA methylation age of human tissues and cell types. Genome Biol, 14(10), R115. doi:10.1186/GB-2013-14-10-r115.

Jylhava, J., Pedersen, N. L., & Hagg, S. (2017). Biological Age Predictors. EBioMedicine, 21, 29-36. doi: 10.1016/j.ebiom.2017.03.046.

Kakushadze, Z., & Yu, W. (2017). *K-means and cluster models for cancer signatures. Biomol Detect Quantif, 13, 7-31. doi:10.1016/j.bdq.2017.07.001.

Kim, S. M., Kim, Y., Jeong, K., Jeong, H., & Kim, J. (2018). Logistic LASSO regression for the diagnosis of breast cancer using clinical demographic data and the BIRADS lexicon for ultrasonography. Ultrasonography, 37(1), 36-42. doi:10.14366/usg.16045.

Kristensen, L. S., Mikeska, T., Krypuy, M., & Dobrovic, A. (2008). Sensitive Melting Analysis after Real Time—Methylation Specific PCR (SMART-MSP): highthroughput and probe-free quantitative DNA methylation detection. Nucleic Acids Res.

Mann, J. J., Ellis, S. P., Waternaux, C. M., Liu, X., Oquendo, M. A., Malone, K. M., . . . Currier, D. (2008). Classification trees distinguish suicide attempters in major psychiatric disorders: a model of clinical decision making. J Clin Psychiatry, 69(1), 23-31.

Marioni, R. E., Harris, S. E., Shah, S., McRae, A. F., von Zglinicki, T., Martin-Ruiz, C., . Deary, I. J. (2018). The epigenetic clock and telomere length are independently associated with chronological age and mortality. Int J Epidemiol, 47(1), 356. doi:10.1093/ije/dyx233.

Monaghan, P. (2010). Telomeres and life histories: the long and the short of it. Ann N Y Acad Sci, 1206, 130-142. doi:10.1111/j.1749-6632.2010.05705.x.

Mupparapu, M., Wu, C. W., & Chen, Y. C. (2018). Artificial intelligence, machine earning, neural networks, and deep learning: Futuristic concepts for new dental diagnosis. Quintessence Int, 49(9), 687-688. doi:10.3290/j.qi.a41107.

Sherbet, G. V., Woo, W. L., & Dlay, S. (2018). Application of Artificial Intelligencebased Technology in Cancer Management: A Commentary on the Deployment of Artificial Neural Networks. Anticancer Res, 38(12), 6607-6613. doi:10.21873/anticanres.13027.

Shi, T., Seligson, D., Belldegrun, A. S., Palotie, A., & Horvath, S. (2005). Tumor classification by tissue microarray profiling: random forest clustering applied to renal cell carcinoma. Mod Pathol, 18(4), 547-557. doi:10.1038/modpathol.3800322.

Svetnik, V., Liaw, A., Tong, C., Culberson, J . C., Sheridan, R. P., & Feuston, B. P. (2003). Random forest: a classification and regression tool for compound classification and QSAR modeling. J Chem Inf Comput Sci, 43(6), 1947-1958. doi:10.1021/ci034160g.

Vetter, V. M., Meyer, A., Karbasiyan, M., Steinhagen-Thiessen, E., Hopfenmuller, W., & Demuth, I. (2018). Epigenetic clock and relative telomere length represent largely different aspects of aging in the Berlin Aging Study II (BASE-II). J Gerontol A Biol Sci Med Sci. doi:10.1093/gerona/gly184.

Yanai, H., Budovsky, A., Tacutu, R., & Fraifeld, V. E. (2011). Is rate of skin wound healing associated with aging or longevity phenotype? Biogerontology, 12(6), 591-597. doi:10.1007/s10522-011-9343-6.

Yu, M., Heinzerling, T. J., & Grady, W. M. (2018). DNA Methylation Analysis Using Droplet Digital PCR. Methods Mol Biol, 1768, 363-383. doi:10.1007/978-1-4939-7778-9_21.

Zhao, Y., Kosorok, M. R., & Zeng, D. (2009). Reinforcement learning design for cancer clinical trials. Stat Med, 28(26), 3294-3315. doi:10.1002/sim.3720.

Jong-Lyul Park et al., Identification and evaluation of age-correlated DNA methylation marker for forensic use, Forensic Science International: Genetics, 2016, pp. 64-70, vol. 23.

A. Freire-Aradas et al., Development of a methylation marker set for forensic age estimation using analysis of public methylation data and the Agena Bioscience EpiTYPER system, Forensic Science International: Genetics, 2016, pp. 65-74, vol. 24.

Jana Naue et al., Chronological age prediction basd on DNA methylation: Massive parallel sequencing and random forest regression, Forensic Science International: Genetics, 2017, pp. 19-28, vol. 31.

Forensic Science International: Genetics, vol. 23, 2016, p. 64-70.

Forensic Science International: Genetics, vol. 24, 2016, p. 65-74.

Forensic Science International: Genetics, vol. 31, 2017, p. 19-28.

* cited by examiner

SEQUENCE LISTING

```
<160> NUMBER OF SEQ ID NOS: 8

<210> SEQ ID NO 1
<211> LENGTH: 266
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 1
cgccctcgcg tccgcggcgt cccctgccgg ccgggcggcg atttgcaggt ccagccggcg        60
ccggtttcgc gcggcggctc aacgtccacg gagccccagg aatacccacc cgctgcccag       120
atcggcagcc gctgctgcgg ggagaagcag tatcgtgcag ggcgggcacg ctggtcttgc       180
ttacagttgg gcttcggtgg gtttgaagca cacattaggg ggaaatggct ctgttcctgc       240
aggtttgcgc agtctgggtt tcttag                                            266

<210> SEQ ID NO 2
<211> LENGTH: 20
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 2
```
aggggagtag ggtaagtgag                                                          20

<210> SEQ ID NO 3
<211> LENGTH: 24
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 3
accatttccc cctaatatat actt                                                     24

<210> SEQ ID NO 4
<211> LENGTH: 20
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 4
gggaggagat ttgtaggttt                                                          20

<210> SEQ ID NO 5
<211> LENGTH: 62
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: misc_feature
<222> LOCATION: (34)..(38)
<223> OTHER INFORMATION: n is a, c, g, or t

<400> SEQUENCE: 5
acactctttc cctacacgac gctcttccga tctnnnnnyg ggyggygatt tgtaggttta      60
gt                                                                             62

<210> SEQ ID NO 6
<211> LENGTH: 58
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 6
gtgactggag ttcagacgtg tgctcttccg atctccctac acratactac ttctcccc      58

<210> SEQ ID NO 7
<211> LENGTH: 45
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 7
aatgatacgg cgaccaccga gatctacact ctttccctac acgac                       45

<210> SEQ ID NO 8
<211> LENGTH: 52
<212> TYPE: DNA
<213> ORGANISM: Artificial Sequence -continued
<220> FEATURE:
<223> OTHER INFORMATION: Description of Artificial Sequence: Synthetic
      polynucleotide

<400> SEQUENCE: 8
caagcagaag acggcatacg agatagtcat cggtgactgg agttcagacg tg                52

EPIAGING ; NOVEL ECOSYSTEM FOR MANAGING HEALTHY AGING

CROSS-REFERENCE TO RELATED APPLICATIONS

This application claims priority under Section 119(e) from U.S. Provisional Application Ser. No. 62/854,226, filed May 29, 2019, entitled "EpiAging; Novel Ecosystem for Managing Healthy Aging" the contents of each which are incorporated herein by reference.

SEQUENCE LISTING

The instant application contains a Sequence Listing which has been submitted electronically in ASCII format and is hereby incorporated by reference in its entirety. Said ASCII copy, created on May 28, 2020, is named TPC57505_Seq List_ST25.txt and is 4,096 bytes in size.

TECHNICAL FIELD

The invention relates to epigenetics and DNA methylation signatures in human DNA generally and in particular, methods of determining the epigenetic aging of an individual and managing healthy aging based on DNA methylation signatures. More specifically, the present invention provides a method involving DNA methylation signatures for molecular diagnostics, health management and lifestyle modification for personalized, healthy aging using App digital technology.

BACKGROUND OF THE INVENTION

Chronological age is understood as the number of years an individual has been alive, whereas biological age, which is also called physiological age denotes how old an individual seems to be. Because people age at different rates it is a challenge to determine the biological age of an individual. Some "look" and "feel" older than their chronological age while others look younger than their chronological age. Although overall human chronological age correlates with biological age, it is not always the case. The biological age is a better parameter of an individual's health, well-being and life span than the chronological age. As an equivalent of the physiological age, the biological age is a reflection of and is influenced by several lifestyle factors including diet, exercise, sleeping habits, etc. But the assessment of the biological age of an individual remains a challenge. Importantly, the need to gauge the true biological age is driven by the thought that it might lead to tests and designs of interventions that will decelerate the rate of biological aging. During the past decades, extensive effort has been invested in identifying different parameters that could predict biological aging and life span such as measures of frailty (Ferrucci et al., 2002), graying of hair, aging of skin (Yanai, Budovsky, Tacutu, & Fraifeld, 2011), levels of different kinds of white blood cells. However, most of these markers were found to offer no advantage over knowing one's chronological age.

More recently, advances in molecular biology have introduced new molecular measures of aging. "Telomere length" (Monaghan, 2010) and "metabolic measures" (Hertel et al., 2016) have been used to predict the biological age. However, although lengths of telomeres vary with age, the correlation between the chronological age and telomere length was found to be weak and the predictive power of life span was low. In addition, the technique used to measure telomere length is technically demanding and technical errors confound the determination of age. Another measure that has been used is the "Metabolic Age score" which measures different metabolites in urine (Hertel et al., 2016). This technique requires a sophisticated method for measurements of different urine ingredients.

A paradigm shift in the search for biological age markers has happened with the discovery of the "epigenetic clock" by Horvath (Horvath, 2013). This clock is based on measurement of DNA methylation clock at 353 CG positions in DNA. It has been found that the extent of methylation of genes included in the methylation clock correlates with one's chronological age better than any previous measure including telomere length, and other aging measures of hair, skin, frailty etc. More importantly, although for most people the DNA methylation clock is very close to the chronological clock, in certain people the clock advances faster than the chronological clock, so that a person could have an epigenetic age that is far older than his chronological clock. Recent studies suggested that such an advancement in the DNA methylation clock predicts early death from different causes. A recent analysis of 13 different studies totaling 13,089 people demonstrated that the epigenetic clock was able to predict all-cause mortality independent of several risk factors such as age, body mass index (BMI), education, smoking, physical activity, alcohol use, smoking and certain comorbidities (Chen et al., 2016).

A recent review by Jylhävä, Pedersen and Hägg in EBiomedicine concluded: "While Telomere length is the most well studied biological age predictor, but many new predictors are emerging, the epigenetic clock is currently the best biological age predictor, as it correlates well with age and predicts mortality (Jylhava, Pedersen, & Hagg, 2017). Technical bias in the measurement of telomere lengths may also contribute to the lack of consistent results." The authors summarize that "Briefly, telomere length is extensively validated but has low predictive power. The composite biomarker is not validated enough but has the potential to be a stronger predictor than telomeres, as is the Metabolic Age Score. The epigenetic clock currently performs the best considering both aspects (Jylhava et al., 2017)."

A comparison of telomere length and epigenetic clock as measures of biological age in the Berlin Aging Study II on 1895 people by Valentin Max Vetter et al., concluded that although "as described previously the telomere length in the younger age group was significantly shorter than in the older age group in the BASE-II cohort, telomere length and chronological age were very weakly negatively correlated in BASE-II (Rs 2=0.013)". In contrast this study found that "Our results showed a positive and significant correlation between DNA methylation (epigenetic clock) age estimation and chronological age R2sRs2=0.47), which persisted after adjustment for covariates (sex, leukocyte distribution, alcohol and smoking)." The authors conclude that: "In summary and as expected, we found DNAm age to be a by far more accurate predictor of chronological age than telomere length (Vetter et al., 2018)."

In a Scottish study of two birth cohorts it was found in a combined cohort analysis that telomere length explained 2.8% of the variance in age while the epigenetic clock explained 34.5% of the variance in age. In the same study, also in a combined cohorts analysis, a one standard deviation increase in baseline epigenetic age was linked to a 25% increased mortality risk while in the same model, a one standard deviation increase in baseline telomere length was independently linked to an 11% decreased mortality risk (P <0.047) (Marion et al., 2018).

Although it is becoming clear that the "epigenetic clock" is the most accurate measure of biological age to date, the tests that are available require testing a large number of sites using blood which is an invasive and costly sample, which is not applicable to a large patient consumer-triggered use. Although available methods are adequate for research and clinical related research, they are not feasible for consumer centered use of this test. Thus, there is a requirement for an accurate, robust, high throughput and noninvasive test.

The present invention provides a solution to the problem in the form of a system of integrating an accurate, robust, saliva-based "EpiAging test" using novel CG sites within an entire health ecosystem for self-learning, self-empowered healthy aging using consumer based and feasible repeated testing of the epigenetic clock integrated with a computer-readable medium alternatively referred to as an Application (App) that enables data collection and communication with the consumer, data sharing and machine learning technologies. Current methods are costly (require DNA methylation of analysis of many CG sites across different genomic regions) and invasive (use blood) and stand alone and provide no guidance for improvement of age scores. Although, general notions of behaviors that have a positive impact on health have been recommended in the medical literature, the exact personalized combination of lifestyle changes that might be of utility to a specific person are unknown. The present invention discloses a system that integrates a consumer based "DNA methylation age test" using saliva with an App-guided health and lifestyle management environment that combines data sharing, machine learning and personalization of health style intervention managed by the consumer through an App. The data is completely blinded and shared only between consumers and no other external party. The incentive for the consumer to share data is the fact that he/she receive a higher quality advice for improving his health by participating in a sharing community, thus the benefit for sharing data is delivered dynamically and repetitively to the consumer by obtaining higher quality of life style assessments and recommendations.

OBJECTIVES OF THE INVENTION

The main objective of the present invention relates to a method for calculating biological age of a subject comprising the steps of extracting DNA from a substrate from a subject, measuring DNA methylation in the extracted DNA from the substrate to obtain a DNA methylation profile, analyzing the DNA methylation profile to obtain a polygenic score, and determining the biological age of the subject from the polygenic score, wherein the extracting DNA comprises extracting genomic DNA from saliva or blood obtained from the subject.

A further objective of the present invention relates to a method for calculating biological age of the subject derived from a polygenic score obtained from a measured DNA methylation profile performed for polygenic DNA methylation biomarkers which comprises measuring the methylation status of CG sites within any one of the human CG sites and combinations thereof, which are positioned in a putative antisense region to ElovL2 gene, the ElovL2 AS1 region as set forth in SEQ ID NO:1.

Another objective of the present invention relates to method for calculating biological age across multiple subjects comprising the steps of extracting DNA from multiple substrates from multiple subjects, measuring DNA methylation in the extracted DNA from multiple substrates to obtain a DNA methylation profile, analyzing the DNA methylation profile to obtain a polygenic score, and determining the biological age across multiple subjects from the polygenic score, wherein extracting DNA comprises extracting genomic DNA from saliva or blood obtained from multiple subjects.

Yet another objective of the present invention relates to a kit for determining the biological age of a subject, comprising the means and reagents for collection and stabilizing of substrate from the subject; a scanner for reading a barcode on the kit; and instructions for collection and stabilizing of the substrate, wherein the substrate is saliva or blood of a subject, and wherein the stabilizing of substrate is for mailing in the collected substrate for extracting DNA for the measurement of DNA methylation in the extracted DNA from the substrate to obtain a DNA methylation profile of the subject to determine the biological age of the subject.

Still another objective of the present invention relates to computer-implemented method for providing recommendations for lifestyle changes, the method comprising the steps of: assessing an entry in a computer-readable medium as obtained through sharing of user data from a subject, matching the said entry to a kit for determining the biological age of a subject as obtained from said subject for determining the biological age of said subject, calculating the biological age of a subject using the method for calculating biological age of a subject or the method for calculating biological age across multiple subjects to obtain the calculated biological age, integrating the said calculated biological age in the machine learning model for said subject by performing statistical analysis using assessment of the entry in a computer-readable medium as obtained through sharing of user data from a subject to obtain an integrated data report, preparing a dynamic report for said subject by analyzing the integrated data report with the progression of responses to the questionnaire as obtained through sharing of user data from said subject with time and comparing them to the recommendations of the national associations, and sharing the dynamic report on the computer-readable medium with said subject for providing recommendations for lifestyle changes.

An alternate object of the present invention relates to method for developing a computer-readable medium, the method comprising the steps of: storing the data derived from multiple subjects, analyzing the stored data, and building a model, wherein the step of storing the data derived from multiple users comprises a cloud-based SQL data base, wherein the step of analyzing the stored data comprises a group selected from deep machine learning, reinforcement learning, and machine learning, or a combination thereof, and wherein the step of building a model comprises correlating input questionnaire measurements and the difference between DNA methylation age and chronological age as an output as well as other physiological and psychological outputs such as pain, blood pressure, BMI and mood.

SUMMARY OF THE INVENTION

Accordingly, the present invention provides methods and materials useful to assess the progression of age, effect of lifestyle, and provide personalized lifestyle recommendations on lifestyle changes based on the calculation of the biological age by a method of analyzing DNA methylation of CG sites or CG positions residing upstream to a gene encoding an antisense mRNA directed against the ElovL2 gene (ElovL2 AS1 region) in substrates from a subject or across multiple subjects in DNA extracted from substrates including blood and saliva.

An embodiment of the present invention relates to a method for calculating biological age of a subject, the method comprising the steps of: extracting DNA from a substrate from the subject, measuring DNA methylation in the extracted DNA from the substrate to obtain a DNA methylation profile, analyzing the DNA methylation profile to obtain a polygenic score, and determining the biological age of the subject from the polygenic score, wherein the extracting DNA comprises extracting genomic DNA from saliva or blood obtained from the subject.

Since, the present invention found that the progression of age is highly correlated with the methylation of CG positions or CG sites that reside or are positioned in the region upstream to a gene encoding an antisense mRNA directed against the ElovL2 gene (called the ElovL2 AS1 region), thus, another embodiment of the present invention relates to the method for calculating biological age of a subject, wherein the method comprises the step of measuring DNA methylation which is performed for polygenic DNA methylation biomarkers which comprises measuring the methylation status of CG sites within any one of the human CG sites as described in Table 1 that provides the CG positions as they appear on the human chromosome 6 as disclosed herein and combinations thereof, which are positioned in a putative antisense region to ElovL2 gene, the ElovL2 AS1 region as set forth in SEQ ID NO:1. The present invention found that the targeted amplicon sequencing of this region revealed the aforementioned 13 novel CG site combination as described in Table 1 that provides the CG positions as they appear on the human chromosome 6 as disclosed herein in the ElovL2 AS1 region as set forth in SEQ ID NO:1, whose methylation was highly correlated with the biological age in saliva. A linear regression equation in the present invention revealed the regression coefficients of these sites with age, where a combined weighted equation of these sites predicts the biological age accurately.

An embodiment of the present invention discloses a method for calculating biological age across multiple subjects, the method comprising the steps of: extracting DNA from multiple substrates from multiple subjects, measuring DNA methylation in the extracted DNA from multiple substrates to obtain a DNA methylation profile, analyzing the DNA methylation profile to obtain a polygenic score, and determining the biological age across multiple subjects from the polygenic score, wherein the extracting DNA comprises extracting genomic DNA from saliva or blood obtained from a subject. The present invention discloses a method that accurately measures DNA methylation age in saliva by determining DNA methylation in a polygenic set of CG sites as described in Table 1 that provides the CG positions as they appear on the human chromosome 6 as disclosed herein in the ElovL2 AS1 region as set forth in SEQ ID NO:1 in hundreds of people concurrently, by sequential amplification with target specific primers followed by barcoding primers and multiplexed sequencing in a single next generation Miseq sequencing reaction, data extraction and quantification of methylation. The present invention also discloses measurement of methylation of the said DNA methylation CG sites as described in Table 1 that provides the CG positions as they appear on the human chromosome 6 as disclosed herein in the ElovL2 AS1 region as set forth in SEQ ID NO:1 using pyrosequencing assays or methylation specific PCR or digital PCR. The present invention discloses the calculation of a polygenic weighted methylation score that predicts age.

An embodiment of the present invention discloses a kit for determining the biological age of a subject, comprising the means and reagents for collection and stabilizing of substrate from the subject; a scanner for reading a barcode on the kit; and instructions for collection and stabilizing of the substrate, wherein the substrate is saliva or blood of a subject, and wherein the stabilizing of substrate is for mailing in the collected substrate for extracting DNA for the measurement of DNA methylation in the extracted DNA from the substrate to obtain a DNA methylation profile of the subject to determine the biological age of the subject.

An embodiment of the present invention discloses a computer-implemented method for providing recommendations for lifestyle changes, the method comprising the steps of: assessing an entry in a computer-readable medium as obtained through sharing of user data from a subject, matching said entry to a kit as disclosed herein, and obtained from the said subject for for determining the biological age of said subject, calculating the biological age of a subject using the method for calculating biological age of a subject as disclosed herein or the method for calculating biological age across multiple subjects to obtain the calculated biological age, integrating the calculated biological age in the machine learning model for said subject by performing statistical analysis using assessment of the entry in a computer-readable medium to obtain an integrated data report, preparing a dynamic report for said subject by analyzing the integrated data report with the progression of responses to the questionnaire as obtained through sharing of user data from said subject with time and comparing them to the recommendations of the national associations, and sharing said dynamic report on the computer-readable medium with said subject for providing recommendations for lifestyle changes. Thus, the present invention discloses the computer-implemented method as disclosed herein, which is a novel process integrating repeated DNA methylation age measurements of the biological age in saliva with dynamic lifestyle changes using a computer-readable medium alternatively referred to as an App that manages these changes. Since the DNA methylation age determination requires only saliva, the disclosed method of the present invention provides with a consumer-initiated ordering of tests through the computer-readable medium or the App, spitting into a saliva collection kit which is mailed to the lab for DNA extraction kit followed by DNA methylation analysis. Lifestyle changes are recorded in the App; methylation data as well as lifestyle data are captured in a database and continuously and iteratively analyzed by machine learning programs such as neural networks.

An embodiment of the present invention discloses a method for developing a computer-readable medium, the method comprising the steps of: storing the data derived from multiple subjects, analyzing the stored data, and building a model, wherein the step of storing the data derived from multiple users comprises a cloud-based SQL data base, wherein the step of analyzing the stored data comprises a group selected from deep machine learning, reinforcement learning, and machine learning, or a combination thereof, and wherein the step of building a model comprises correlating input questionnaire measurements and the difference between DNA methylation age and chronological age as an output as well as other physiological and psychological outputs such as pain, blood pressure, BMI and mood. Multiple consumers shared data is continuously analyzed to build the model that relates input lifestyle changes with the output of difference between DNA methylation age or the biological age as provided by the method as disclosed in the present invention and the chronological age. The model as disclosed herein is applied to personal data and the model derives recommendations on personal changes in lifestyle. Input lifestyle changes and output DNA methylation age or the biological age as disclosed herein are iteratively measured and used for further reinforcement learning with additional advice beamed to the Apps of the consumers.

The present invention provides methods that could be used by any person skilled in the art to measure biological age and the relationship between lifestyle changes and DNA methylation age. The DNA methylation markers (CGIDs) as described in Table 1 that delineates the selected CG positions in the upstream region in the human chromosome 6 in the newly found gene ElovL2 AS1 as set forth in SEQ ID NO:1 as disclosed herein described in the present invention are useful for consumer-initiated saliva-based tests for determining DNA methylation aging or the biological age and for reporting and modification of lifestyle parameters using a "shared" App or the computer-readable medium and machine learning system. The present invention is demonstrated to be useful in measuring the "biological age" using polygenic score based on the DNA methylation measurement methods disclosed herein, which include targeted amplicon sequencing of the antisense ELOVL2 AS1 region as set forth in SEQ ID NO:1 disclosed herein across hundreds of individuals or subjects concurrently or by using other methods for measuring DNA methylation available to people skilled in the art such as next generation bisulfite sequencing, pyrosequencing, MeDip sequencing, ion torrent sequencing, Illumina 450 K arrays and Epic microarrays etc. The present invention also discloses the utility of the present invention for integrating DNA methylation measurements within a comprehensive plan for life style changes using the "EpiAging" App disclosed herein which could be developed by anyone skilled in the art using open source and other programs such as Build Fire JS, Ionic, Appcelerator's Titanium SDK, Mobile angular UI, and Siberian CMS. Data will be stored in a data base such as MySQL in a cloud server such as Azure Cloud or Amazon cloud which could be handled by anyone skilled in the art. The data will be analyzed by a machine-learning platform such as Neural networks using open source programs such as Tensor flow or R statistics available to people skilled in the art. The present invention discloses the utility of the present invention in providing customers with dynamic "personalized" reports with recommendations for a combination of lifestyle changes that might impact their healthy aging. The present invention also discloses the utility of the "EpiAging" DNA methylation test and App for measuring the impact of the interventions on their biological age by sending saliva for measuring DNA methylation age before and following recommended lifestyle changes.

Other objects, features and advantages of the present invention will become apparent to those skilled in the art from the following detailed description. It is to be understood, however, that the detailed description and specific examples, while indicating some embodiments of the present invention, are given by way of illustration and not limitation. Many changes and modifications within the scope of the present invention may be made without departing from the spirit thereof, and the invention includes all such modifications.

DETAIL DESCRIPTIONS OF THE INVENTION

Figure 1:
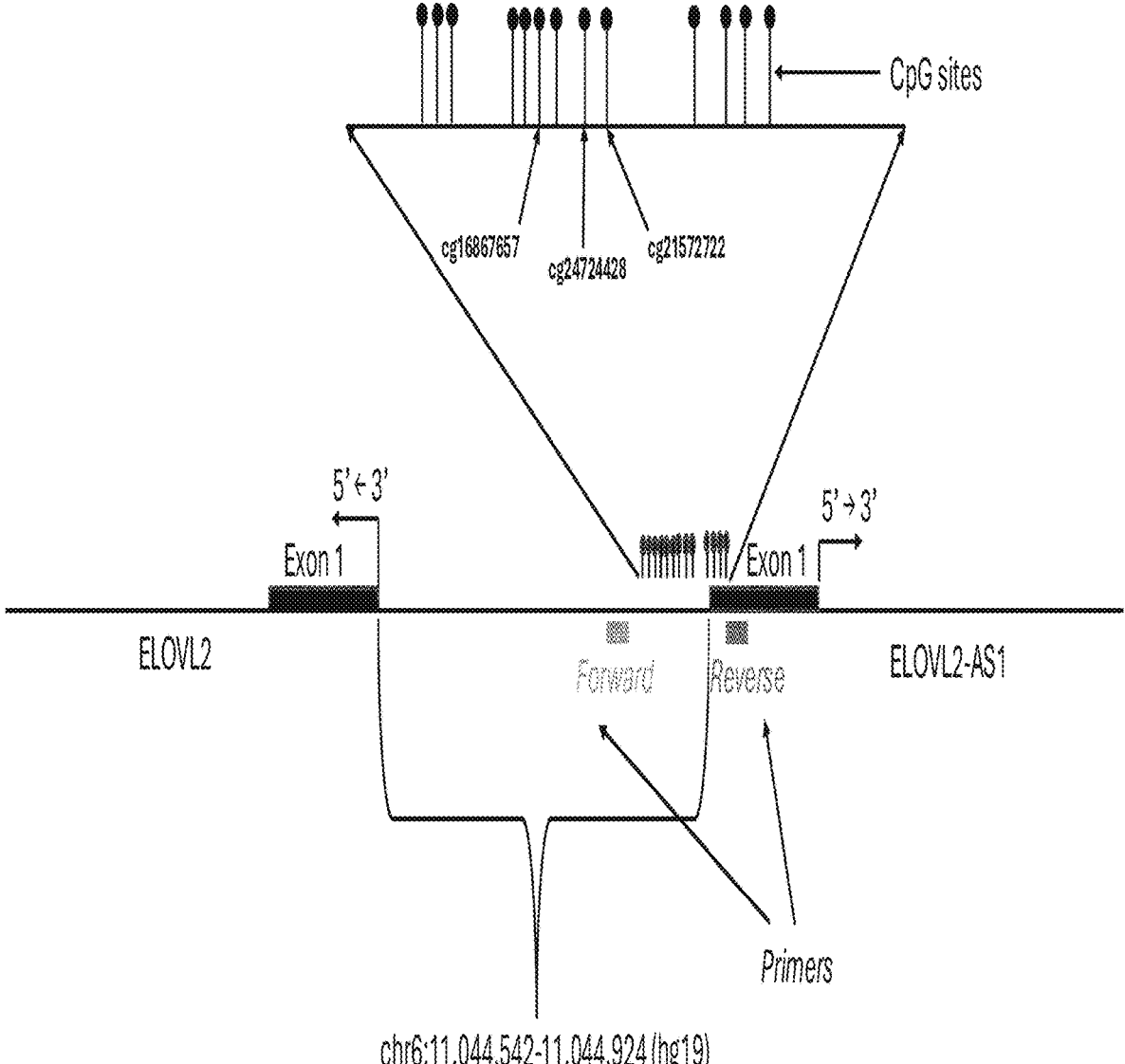
FIG. 1. As DNA methylation at CG sites in antisense region upstream of ElovL2 gene, referred to as the ElovL2 AS1 region correlates with age. The IGV browser view of the human genomic region around the CG sites and the position of the two CGs the ElovL2 AS1 region, namely, cg16867657 and cg21572722 as described in Table 1 disclosed herewith is depicted. A Pearson correlation between states of methylation of CGIDs across the genome in blood cells in publicly available Illumina450K arrays and age revealed that the top CG was cg16867657 with a Pearson product-moment correlation coefficient r=0.934 (p=0) and a neighboring site cg21572722 whose correlation coefficient with age was r=0.81004 (p=0) depicting that the methylation state of the discovered CG sites correlates with age in the ElovL2 AS1 region. Examination of the genomic position of this CG revealed that it is a member of a sequence of 13 CGs (indicated) that reside in a previously uncharacterized region, the ElovL2 antisense gene ElovL2 AS1 region.

In the description of embodiments, reference may be made to the accompanying figures which form a part hereof, and in which is shown by way of illustration a specific embodiment in which the invention may be practiced. It is to be understood that other embodiments may be utilized and structural changes may be made without departing from the scope of the present invention. Many of the techniques and procedures described or referenced herein are well understood and commonly employed by those skilled in the art. Unless otherwise defined, all terms of art, notations and other scientific terms or terminology used herein are intended to have the meanings commonly understood by those of skill in the art to which this invention pertains. In some cases, terms with commonly understood meanings are defined herein for clarity and/or for ready reference, and the inclusion of such definitions herein should not necessarily be construed to represent a substantial difference over what is generally understood in the art.

All illustrations of the drawings are for the purpose of describing selected versions of the present invention and are not intended to limit the scope of the present invention.

All publications mentioned herein are incorporated herein by reference to disclose and describe aspects, methods and/or materials in connection with the cited publications.

DNA methylation refers to chemical modifications of the DNA molecule. Technological platforms such as the Illumina Infinium microarray or DNA sequencing-based methods have been found to lead to highly robust and reproducible measurements of the DNA methylation levels of a person. There are more than 28 million CpG or CG loci in the human genome. Consequently, certain loci are given unique identifiers such as those found in the Illumina CpG or CG loci database. These CG locus designation identifiers are used herein.

Definitions

As used herein, the term "CG" refers to a di-nucleotide sequence in DNA containing cytosine and guanosine bases. The CG position referred to as "CG sites" as used herein, are positions in the human genome is defined by chromosome and nucleotide position in the reference human genome hg19.

As used herein, the term "beta-value" refers to computation of methylation level at a CGID position derived by normalization and quantification of Illumina 450K or EPIC arrays using the ratio of intensities between methylated and unmethylated probes and the formula: beta value= methylated C intensity/(methylated C intensity+unmethylated C intensity) between 0 and 1 with 0 being fully unmethylated and 1 being fully methylated.

As used herein, the term "Decision Trees" is a type of data mining algorithm that selects from many variables and the interactions between variables those that most predict the response or outcome to be explained (Mann et al., 2008).

As used herein, the term "Random Forests" is a type of data mining algorithm that can select the most important variables in determining the given outcome or response (Shi, Seligson, Belldegrun, Palotie, & Horvath, 2005; Svetnik et al., 2003).

As used herein, the term "Lasso regression" is a method for selection of variables for linear regression models which identifies the minimal subset of predictors that are needed to predict an outcome (a response variable) with the minimized prediction error (Kim, Kim, Jeong, Jeong, & Kim, 2018).

As used herein, the term "K-means cluster analysis" is an unsupervised machine learning method that partitions observations into a smaller set of clusters where each observation belongs to one cluster (Beauchaine & Beauchaine, 2002; Kakushadze & Yu, 2017).

As used herein, the term "Reinforcement Learning" involves receiving feedback from data analysis and learning through trial and error. A sequence of successful decisions will result in reinforcement of a process (Zhao, Kosorok, & Zeng, 2009).

As used herein, the term "penalized regression" refers to a statistical method aimed at identifying the smallest number of predictors required to predict an outcome out of a larger list of biomarkers as implemented for example in the R statistical package "penalized" as described in Goeman, J. J., L1 penalized estimation in the Cox proportional hazards model. Biometrical Journal 52(1), 70-84.

As used herein, the term "clustering" refers to the grouping of a set of objects in such a way that objects in the same group (called a cluster) are more similar (in some sense or another) to each other than to those in other groups (clusters).

As used herein, the term "Neural Networks and deep learning" refer to a method of machine learning that incorporates neural networks in several layers to learn from data in an iterative manner. A neural network looks at the different data inputs such as lifestyle variables as collection of connected units or nodes called artificial neurons, which have multiple interactions like neurons in a brain (De Roach, 1989; Mupparapu, Wu, & Chen, 2018; Sherbet, Woo, & Dlay, 2018). These interactions drive the output of biological aging measured as accelerated or decelerated relative to chronological age.

As used herein, the term "multiple or polygenic linear regression" refers to a statistical method that estimates the relationship between multiple "independent variables" or "predictors" such as percentage of methylation in multiple CG IDs, and a "dependent variable" such as chronological age. This method determines the "weight" or coefficient of each CG IDs in predicting the "outcome" (dependent variable such as age) when several "independent variables" such as CG IDs are included in the model.

As used herein, the term "Pearson correlation" refers to a statistical method that estimates the correlation between an "independent variable" or "predictor" such as percentage of methylation in a CG ID, and a "dependent variable" such as chronological age. The Pearson product-moment correlation coefficient r quantitatively weighs the correlation between 0 indicating no correlation and 1 indicating perfect correlation (Hardy & Magnello, 2002).

The presently disclosed method is based on the discovery of sites in the human genome whose methylation state correlates with age, which were discovered by performing a series of Pearson correlation between age and DNA methylation across 450K sites in the genome in available public data sets (GSE61496, GSE98876) and validated the so discovered DNA methylation markers using data from GSE40729. The analysis identified cg16867637 as the top site correlated with age (r=0.934827, p=0). The present invention discovered a fragment of the human genome on chromosome 6 which is an antisense sequence to previously described age-related ElovL2 gene, the ElovL2 AS1 region that contains 13 CGs referred to as CG sites herein, are the positions of the di-nucleotide sequence as described hereinbelow in Table 1 as disclosed herein, whose combined methylation measures, computed in a multiple liner regression equation provide a polygenic score of the biological age in saliva with higher accuracy than previously reported positions in the genome. These sites were previously not described, as they were not included in Illumina arrays. Thus, the present invention discloses novel CG sites whose combined weighted methylation levels correlate with age. The present invention further demonstrates herein that the methylation of all 13 CG sites can be accurately measured by amplifying a single amplicon and using indexed next generation sequencing to measure hundreds of people at the same time, thus reducing cost and increasing throughput, by using the "EpiAging" test as disclosed herein. The subject or the customer orders a saliva collection kit, spits into the kit collecting tube and sends the kit back to the lab where DNA is extracted, converted by bisulfite and the ElovL2 AS1 region is amplified and indexed. Amplicons from 200 subjects are sequenced in the same Miseq reaction. FastQ files are analyzed and methylation level at 13 CG sites is determined. Using an equation that correlates the weighted methylation values of the 13 CG sites and age, the biological age is calculated and shared with the customer.

The present invention further discloses and addresses the utility of the presently disclosed methods in calculating the biological age in a dynamic manner so as to improve the healthy aging of the customer by recommending lifestyle changes. The present invention discloses that effective interventions can be derived from "machine learning" of the relationship between multiple lifestyle variables and the difference between DNA methylation age and biological changes. As lifestyle data and methylation age data or biological age are dynamically collected from multiple subjects/users, the machine learns how combination of changes in lifestyle parameters are related to increasing or decreasing difference between DNA methylation and biological age. The present invention integrates DNA methylation test with subject/consumer-focused sharing, learning and lifestyle modifications. The subject/consumer orders and communicates his lifestyle decisions using the EpiAging App or the computer-readable medium as disclosed herein in the present invention. Improving health is a bidirectional partnership and a collaborative effort and not a unidirectional flow of instructions from the "learned omniscient" health professional (health provider) to the "obedient" and passive patient (health consumer). The best advice from science as distilled from the most reputable national medical associations is presented to the consumer using the EpiAging App. The consumer decides which recommendations to act upon. The consumer shares the decisions using a "fully blinded" App. The consumer receives an ID which is linked to his mobile ID but "fire walled" from personal information such as address, name, e-mail etc. The personal interventions and outcomes of multiple users are analyzed repeatedly as well as DNA methylation age test results, integrating both physical and mental outcomes. The data is analyzed using state of the art machine learning algorithms such as neural networks, using for example Tensor Flow. A model correlating the different input parameters with the output delta between DNA methylation age and chronological age is established. The personal data of a consumer is used with the model and suggestions for adjustment are personalized and delivered to the consumer. The present invention provides a grand platform for transpiring a science inspired perpetually progressing, dynamic recommendation model. The present invention proposes an "evolutionary" platform which dynamically improves with use with an ever-expanding body of data. Both customer's well-being as well as the learning-environment coevolve in a dynamic interplay between DNA methylation tests, lifestyle modifications, shared data and machine learning as disclosed in the present invention.

The invention disclosed herein has a number of embodiments. In an aspect of the present invention, the present invention provides polygenic DNA methylation markers of biological age for life style management of healthy aging, said polygenic DNA methylation markers set is derived using Pearson correlation analysis of the correlation between age and DNA methylation across the genome on genome wide DNA methylation derived by mapping methods, such as Illumina 450K or 850K arrays, genome wide bisulfite sequencing using a variety of next generation sequencing platforms, methylated DNA Immunoprecipitation (MeDIP) sequencing or hybridization with oligonucleotide arrays or a combination of these method.

In one embodiment, the present invention provides a method for calculating biological age of a subject, the method comprising the steps of: (a) extracting DNA from a substrate from the subject; (b) measuring DNA methylation in the extracted DNA from the substrate to obtain a DNA methylation profile; (c) analyzing the DNA methylation profile to obtain a polygenic score; and (d) determining the biological age of the subject from the polygenic score, wherein the extracting DNA comprises extracting genomic DNA from saliva or blood obtained from the subject. The method for calculating biological age of a subject as disclosed herein, wherein the measuring DNA methylation is performed using methods comprising, DNA pyrosequencing, mass spectrometry based (Epityper™), PCR based methylation assays, targeted-amplicon next generation bisulfite sequencing on a platform selected from a group of HiSeq, MiniSeq, MiSeq, and NextSeq sequencers, Ion Torrent sequencing, methylated DNA Immunoprecipitation (MeDIP) sequencing, or hybridization with oligonucleotide arrays. The method for calculating biological age of a subject as disclosed herein, wherein the measuring DNA methylation is performed for polygenic DNA methylation biomarkers which comprises measuring the methylation status of CG sites within any one of the human CG sites and combinations thereof are the positions of the di-nucleotide sequence as described hereinbelow in Table 1 as disclosed herein, which are positioned in the antisense region to ElovL2 gene in human chromosome 6, the ElovL2 AS1 region as set forth in SEQ ID NO:1 (CGCCCTCG CGTCCGCGGCGTCCCCTGCCGGCCGGGCGGCGAT-TTGCAGGTCC AGCCGGCGCCGGTTTCGCGCGG CG G CTCAACGTCCACGGAGCCCCAGGAATA CCCA CCCGCTGCCCAGATCGGCAGCCGCTGCTGCGGG-GAGAAGCAGTATCGT GCAGGGCGGGCAC GCTG GTCTTGCTTACAGTTGGGCTTCGGTGGGTTTGAAG CACACATTAGGGGGAAATGGCTCTGTTCCTGCAGG TTTGCGCAGTCTGGGTTT CTTAG).

The position in the human genome for the selected 13 CG di-nucleotide in the CG sites as used in various embodiments herein are found in Table 1 that is included with this application, which also provides the CG position in chromosome 1 as used in Figures and Examples of this application.

TABLE 1

Positions having CG Methylation Sites (CG sites)
corresponding to the 13 CG sites upstream of antisense
ElovL2 gene, the ElovL2 AS1 region as set forth in SEQ
ID NO: 1 and useful in embodiments of the present invention.

| Illumina 450K CGID | Human Chromosome | Start Position | End Position | Sequence |
|---|---|---|---|---|
| cg16867657 | Chromosome 6 | 11044877 | 11044878 | CG |
| cg21572722 | Chromosome 6 | 11044894 | 11044895 | CG |
| NA* | Chromosome 6 | 11044861 | 11044862 | CG |
| NA* | Chromosome 6 | 11044864 | 11044865 | CG |
| NA* | Chromosome 6 | 11044867 | 11044868 | CG |
| NA* | Chromosome 6 | 11044873 | 11044874 | CG |
| NA* | Chromosome 6 | 11044875 | 11044876 | CG |
| NA* | Chromosome 6 | 11044880 | 11044881 | CG |
| NA* | Chromosome 6 | 11044888 | 11044889 | CG |
| NA* | Chromosome 6 | 11044916 | 11044917 | CG |
| NA* | Chromosome 6 | 11044928 | 11044929 | CG |
| NA* | Chromosome 6 | 11044935 | 11044936 | CG |
| NA* | Chromosome 6 | 11044943 | 11044944 | CG |
| cg09809672 | Chromosome 1 | 236557682 | 236557683 | CG |

*NA means not available

In one embodiment, the present invention provides a method for calculating biological age of a subject, the method comprising the steps of: (a) extracting DNA from a substrate from the subject; (b) measuring DNA methylation in the extracted DNA from the substrate to obtain a DNA methylation profile; (c) analyzing the DNA methylation profile to obtain a polygenic score; and (d) determining the biological age of the subject from the polygenic score, wherein the extracting DNA comprises extracting genomic DNA from saliva or blood obtained from the subject, wherein the measuring DNA methylation is performed using DNA pyrosequencing comprising primers as set forth in SEQ ID NO:2 (AGGGGAGTAGGGTAAGTGAG) for the forward, biotinylated, primer, SEQ ID NO:3 (ACCAT-TTCCCCCTAATATATACTT) for the reverse primer, and SEQ ID NO:4 (GGGAGGAGATTTGTAGGTTT) for the pyrosequencing primer.

In one embodiment, the present invention provides use of DNA pyrosequencing methylation assays for DNA methylation age using the ElovL2 AS1 region containing the CG sites and combinations thereof are the positions of the di-nucleotide sequence as described in Table 1 as disclosed herein, using the primers as disclosed herein and standard conditions of pyrosequencing reactions recommended by the manufacturer (Pyromark, Qiagen), wherein the primers comprise a Forward (biotinylated) primer as set for the in SEQ ID NO:2, an Elovl2_Rv primer as set forth in SEQ ID NO:3, and an Elovl2_Seq primer as set forth in SEQ ID NO:4.

In one embodiment, the present invention provides a method for calculating biological age of a subject, the method comprising the steps of: (a) extracting DNA from a substrate from the subject; (b) measuring DNA methylation in the extracted DNA from the substrate to obtain a DNA methylation profile; (c) analyzing the DNA methylation profile to obtain a polygenic score; and (d) determining the biological age of the subject from the polygenic score, wherein the extracting DNA comprises extracting genomic DNA from saliva or blood obtained from the subject, wherein the measuring DNA methylation is performed using targeted-amplicon next generation bisulfite sequencing on a platform selected from a group of HiSeq, MiniSeq, MiSeq, and NextSeq sequencers, comprising primers as set forth in SEQ ID NO:5 (ACACTCTTTCCCTACACGACGC TCTTCCGATCTNNNNNYGGGYGGYGATTTG TA GGTTTAGT) for the forward primer and SEQ ID NO:6 (GTGACTGGAGTTCAGACGTGTGCTCTTCC-GATCTCCCTACACRATACTACTTC TCCCC) for the reverse primer.

In one embodiment, the present invention provides use of polygenic multiplexed amplicon bisulfite sequencing DNA methylation assay for measuring DNA methylation age in saliva by using ElovL2 AS1 region containing the CG sites and combinations thereof are the positions of the di-nucleotide sequence as described in Table 1 as disclosed herein, using the primers as disclosed herein and standard conditions that involve bisulfite conversion, sequential amplification comprising the use of: (a) target specific primers (PCR 1) and (b) barcoding primers (PCR 2) and multiplexed sequencing in a single next generation Miseq sequencer (Illumina), demultiplexing using Illumina software, data extraction and quantification of methylation using standard methods for methylation analysis including the Methylkit, followed by calculation of the weighted DNA methylation score for calculation of the biological age of a subject, wherein the target specific primers (PCR 1) are as set forth in SEQ ID NO:5 (ACACTCTTTCCCTACACG ACGCTCTTCCGATCTNNNNNYGGGYGGYGATTTG TAGGTTTAGT) for the forward primer and SEQ ID NO:6 (GTGACTGGAGTTCAGACGTGTGCTCTTCCGAT CTCCCTACACRATACTACTTC TCCCC) for the reverse primer, and wherein the barcoding primers (PCR 2) are as set forth in SEQ ID NO:7 (AATGATACGGCGAC-CACCGAGATCTACACTCTTTCCCTACACGAC) for the forward primer and SEQ ID NO:8 (CAAGCAGAA-GACGGCATACGAGATAGTCATCGGTGACTGGAG TTCAGACGT G) for the reverse primer, which is the barcode index primer. In the SEQ ID NO:5 as disclosed herein, ACACTCTTTCCCTACACGACGCTCTTCCGAT CTNNNNNYGGGYGG YGATTTGT AGGTTTAGT , black bases are adapters and red bases are targeted sequences. In the SEQ ID NO:6 as disclosed herein, GTGACTGGAGTTCAGACGTGTGCTCTTCCGATCT CCCTACACRATACTACTTC TCCCC , black bases are adapters and red bases are targeted sequences. In the SEQ ID NO:8 as disclosed herein, the barcoding primer, CAAGCAGAAGACGGCATACGAGAT AGTCATCG GTGACTGGAGTTCAGACGTG, red bases are the index; up to 200 variations of this index are used.

In one embodiment, the present invention provides a method for calculating biological age of a subject, the method comprising the steps of: (a) extracting DNA from a substrate from the subject; (b) measuring DNA methylation in the extracted DNA from the substrate to obtain a DNA methylation profile; (c) analyzing the DNA methylation profile to obtain a polygenic score; and (d) determining the biological age of the subject from the polygenic score, wherein the measuring DNA methylation is performed using PCR based methylation assays selected from a group of methylation specific PCR and digital PCR.

In one embodiment, the present invention provides a method for calculating biological age of a subject, the method comprising the steps of: (a) extracting DNA from a substrate from the subject; (b) measuring DNA methylation in the extracted DNA from the substrate to obtain a DNA methylation profile; (c) analyzing the DNA methylation profile to obtain a polygenic score; and (d) determining the biological age of the subject from the polygenic score, wherein the analyzing the DNA methylation profile to obtain a polygenic score comprises using multiple linear regression equations or neural network analysis.

In one embodiment, the present invention provides a method for calculating biological age across multiple subjects, the method comprising the steps of: (a) extracting DNA from multiple substrates from multiple subjects; (b) measuring DNA methylation in the extracted DNA from multiple substrates to obtain a DNA methylation profile; (c) analyzing the DNA methylation profile to obtain a polygenic score; and determining the biological age across multiple subjects from the polygenic score, wherein the extracting DNA comprises extracting genomic DNA from saliva or blood obtained from a subject.

In one embodiment, the present invention provides a method for calculating biological age across multiple subjects, the method comprising the steps of: (a) extracting DNA from multiple substrates from multiple subjects; (b) measuring DNA methylation in the extracted DNA from multiple substrates to obtain a DNA methylation profile; (c) analyzing the DNA methylation profile to obtain a polygenic score; and determining the biological age across multiple subjects from the polygenic score, wherein the extracting DNA comprises extracting genomic DNA from saliva or blood obtained from a subject, and wherein the measuring the DNA methylation in the extracted DNA from multiple substrates comprises the steps of: (i) amplifying genomic DNA extracted from the multiple substrates with target specific primers to obtain PCR product 1; (ii) amplifying the PCR product 1 of step (i) by barcoding primers to obtain PCR product 2; (iii) performing multiplexed sequencing in a single next generation Miseq sequencing reaction using the PCR product 2 of step (ii); (iv) extracting data from the multiplexed sequencing of step (iii); and quantifying DNA methylation from the extracted data of step (iv) to obtain a DNA methylation profile for each substrate. In an alternate embodiment, the present invention provides a method for calculating biological age across multiple subjects, wherein the target specific primers to obtain PCR product 1 comprises primers as set forth in SEQ ID NO:5 (ACA CTCTTTCCCTACACGACGCTCTTCCGATCTNNNN- NYGGGYGGYGATTTG TAGGTTTAGT) for the forward primer and SEQ ID NO:6 (GTGACTGGAGTTCA- GACGTGTGCTCTTCCGATCTCCCTACACRATAC- TACTTC TCCCC) for the reverse primer, and wherein barcoding primers to obtain PCR product 2 comprises primers as set forth in SEQ ID NO:7 (AATGA- TACGGCGACCACCGAGATCTACACTCTTTCCCTA- CACGAC) for the forward primer and SEQ ID NO:8 (CAAGCAGAAGACGGCATACGAGATAGTCATC GGTGACTGGAGTTCAGACGT G) for the reverse primer, which is the barcode index primer.

In one embodiment, the present invention provides a combination of DNA methylation biomarkers for calculating biological age, wherein the combination of the of DNA methylation biomarkers comprises the human CG sites and combinations thereof, which are positioned in a putative antisense region to ElovL2 gene, the ElovL2 AS1 region as set forth in SEQ ID NO:1. In one embodiment of the present invention, 13 CG sites positioned in a putative antisense region to ElovL2 gene, ElovL2 AS1 region as set forth in SEQ ID NO:1 that could be used alone or in combination as measures of biological age are delineated. In one embodiment, the present invention provides use of CG sites and combinations thereof are the positions of the di-nucleotide sequence as described in Table 1 as disclosed in the present invention.

In one embodiment, the present invention provides a kit for determining the biological age of a subject, comprising the means and reagents for collection and stabilizing of substrate from the subject; a scanner for reading a barcode on the kit; and instructions for collection and stabilizing of the substrate, wherein the substrate is saliva or blood of a subject, and wherein the stabilizing of substrate is for mailing in the collected substrate for extracting DNA for the measurement of DNA methylation in the extracted DNA from the substrate to obtain a DNA methylation profile of the subject to determine the biological age of the subject. In an alternate embodiment, the present invention provides a kit for determining the biological age of a subject, wherein the kit is a saliva collection kit, which the customer or subject orders, spits into the kit collecting tube, which is mailed to the lab by a DNA extraction kit followed by DNA methylation analysis. In one embodiment, the present invention provides a kit for collecting saliva samples from customers comprising means and reagents for collection and stabilizing of saliva from customers. In one embodiment, the present invention provides a kit comprising means and reagents for DNA methylation measurements of the CG sites and combinations thereof are the positions of the di-nucleotide sequence as described in Table 1 as disclosed herein.

In one embodiment, the present invention provides an Application (App) for management of DNA methylation age testing ordering, submission, receiving test results and management of lifestyle. In one embodiment, an App is developed using open source development tools to contain information on the test, a virtual shopping cart for ordering the test, a scanning function for scanning the saliva kit barcode and a function for receiving test results from the lab. In one embodiment, the present invention provides questionnaires to be included in the App that will probe life style functions that might impact on "healthy aging", these include basic physiological measures, weight, height blood pressure, heart rate, etc. mood self-assessment, McGill pain questionnaire, diet and nutrition questionnaire, exercise questionnaire and lifestyle question such as alcohol, drugs and smoking. In one embodiment, the method comprises of performing statistical analysis on the response to the questionnaires and providing a dynamic report to the consumers on the App that describes the progression of responses to the questionnaire with time as compared to recommendations of the national associations such as Cancer, heart and Stroke and diabetes.

In one embodiment, the present invention provides for storing the data derived from multiple users in a cloud-based SQL data base and using "machine learning" for analysis of the data and building a model correlating input questionnaire measurements and the difference between DNA methylation age and chronological age as an output as well as other physiological and psychological outputs such as pain, blood pressure, BMI and mood. In a further embodiment, the present invention as disclosed herein wherein, machine learning is selected from a group of "deep machine learning" data mining methods includes neural networks or "reinforcement learning" through feedback from consumers is utilized to reinforce the most effective lifestyle changes, or "machine learning" data mining algorithm includes "random forest" analysis, or "machine learning" data mining algorithm includes K-Means Cluster Analysis, or "machine learning" platform includes Amazon Machine Learning (AML), or "machine learning" software includes H2O.ai products on platforms such as Apache Hadoop Distributed File system, Amazon EC2 Google compute Engine and Microsoft Azure.

In one embodiment, the present invention provides a computer-implemented method for providing recommendations for lifestyle changes, the method comprising the steps of: (a) assessing an entry in a computer-readable medium as obtained through sharing of user data from a subject; (b)

matching the entry of step (a) to a kit for determining the biological age of a subject, comprising the means and reagents for collection and stabilizing of substrate from the subject; a scanner for reading a barcode on the kit; and instructions for collection and stabilizing of the substrate, wherein the substrate is saliva or blood of a subject, and wherein the stabilizing of substrate is for mailing in the collected substrate for extracting DNA for the measurement of DNA methylation in the extracted DNA from the substrate to obtain a DNA methylation profile of the subject to determine the biological age of said subject; (c) calculating the biological age of a subject using the method comprising: (i) extracting DNA from a substrate from the subject; (ii) measuring DNA methylation in the extracted DNA from the substrate to obtain a DNA methylation profile; (iii) analyzing the DNA methylation profile to obtain a polygenic score; and (iv) determining the biological age of the subject from the polygenic score, wherein the extracting DNA comprises extracting genomic DNA from saliva or blood obtained from a subject to obtain the calculated biological age; (d) integrating the calculated biological age of step (c) in the machine learning model for said subject by performing statistical analysis using assessment of step (a) to obtain an integrated data report; (e) preparing a dynamic report for said subject by analyzing the integrated data report of step (d) with the progression of responses to the questionnaire as obtained through sharing of user data from said subject with time and comparing them to the recommendations of the national associations; and (f) sharing the dynamic report of step (e) on the computer-readable medium with said subject for providing recommendations for lifestyle changes. In a further embodiment, the present invention provides a computer-implemented method for providing recommendations for lifestyle changes, wherein the computer-readable medium comprises open source development tools to contain information on a test for calculating biological age based on the method as disclosed herein, a virtual shopping cart for ordering said test, a scanning function for scanning a barcode of the kit of for determining the biological age of a subject as disclosed herein, a function for receiving test results from the lab, and wherein the open source development tools comprise questionnaires included in the computer-readable medium to probe lifestyle functions that impact on healthy aging, including basic physiological measures, weight, height blood pressure, heart rate, mood self-assessment, McGill pain questionnaire, diet and nutrition questionnaire, exercise questionnaire and lifestyle question including alcohol, drugs and smoking, and combination thereof.

In an alternate embodiment, the present invention provides computer-implemented method for providing recommendations for lifestyle changes, the method comprising the steps of: (a) assessing an entry in a computer-readable medium as obtained through sharing of user data from a subject; (b) matching the entry of step (a) to a kit for determining the biological age of a subject, comprising the means and reagents for collection and stabilizing of substrate from the subject; a scanner for reading a barcode on the kit; and instructions for collection and stabilizing of the substrate, wherein the substrate is saliva or blood of a subject, and wherein the stabilizing of substrate is for mailing in the collected substrate for extracting DNA for the measurement of DNA methylation in the extracted DNA from the substrate to obtain a DNA methylation profile of the subject to determine the biological age of said subject; (c) calculating the biological age of a subject using the method comprising: (i) extracting DNA from multiple substrates from multiple subjects; (ii) measuring DNA methylation in the extracted DNA from multiple substrates to obtain a DNA methylation profile; (iii) analyzing the DNA methylation profile to obtain a polygenic score; (iv) determining the biological age across multiple subjects from the polygenic score, wherein the extracting DNA comprises extracting genomic DNA from saliva or blood obtained from a subject to obtain the calculated biological age; (d) integrating the calculated biological age of step (c) in the machine learning model for said subject by performing statistical analysis using assessment of step (a) to obtain an integrated data report; (e) preparing a dynamic report for said subject by analyzing the integrated data report of step (d) with the progression of responses to the questionnaire as obtained through sharing of user data from said subject with time and comparing them to the recommendations of the national associations; and (f) sharing the dynamic report of step (e) on the computer-readable medium with said subject for providing recommendations for lifestyle changes. In a further embodiment, the present invention provides a computer-implemented method for providing recommendations for lifestyle changes, wherein the computer-readable medium comprises open source development tools to contain information on a test for calculating biological age based on the method as disclosed herein, a virtual shopping cart for ordering said test, a scanning function for scanning a barcode of the kit of for determining the biological age of a subject as disclosed herein, a function for receiving test results from the lab, and wherein the open source development tools comprise questionnaires included in the computer-readable medium to probe lifestyle functions that impact on healthy aging, including basic physiological measures, weight, height blood pressure, heart rate, mood self-assessment, McGill pain questionnaire, diet and nutrition questionnaire, exercise questionnaire and lifestyle question including alcohol, drugs and smoking, and combination thereof.

In yet another alternate embodiment, the present invention provides computer-implemented method for providing recommendations for lifestyle changes, the method comprising the steps of: (a) assessing an entry in a computer-readable medium as obtained through sharing of user data from a subject; (b) matching the entry of step (a) to a kit for determining the biological age of a subject, comprising the means and reagents for collection and stabilizing of substrate from the subject; a scanner for reading a barcode on the kit; and instructions for collection and stabilizing of the substrate, wherein the substrate is saliva or blood of a subject, and wherein the stabilizing of substrate is for mailing in the collected substrate for extracting DNA for the measurement of DNA methylation in the extracted DNA from the substrate to obtain a DNA methylation profile of the subject to determine the biological age of said subject; (c) calculating the biological age of a subject using the method comprising: (i) extracting DNA from multiple substrates from multiple subjects; (ii) measuring DNA methylation in the extracted DNA from multiple substrates to obtain a DNA methylation profile; (iii) analyzing the DNA methylation profile to obtain a polygenic score; (iv) determining the biological age across multiple subjects from the polygenic score, wherein the extracting DNA comprises extracting genomic DNA from saliva or blood obtained from a subject to obtain the calculated biological age, wherein the measuring DNA methylation in the extracted DNA from multiple substrates comprises the steps of: (1) amplifying genomic DNA extracted from the multiple substrates with target specific primers to obtain PCR product 1; (2) amplifying the PCR product 1 of step (1) by barcoding primers to obtain PCR product 2; (3) performing multiplexed sequencing in a single next generation Miseq sequencing reaction using the PCR product 2 of step (2); (4) extracting data from the multiplexed sequencing of step (3); (5) quantifying DNA methylation from the extracted data of step (d) to obtain a DNA methylation profile for each substrate; (d) integrating the calculated biological age of step (c) in the machine learning model for said subject by performing statistical analysis using assessment of step (a) to obtain an integrated data report; (e) preparing a dynamic report for said subject by analyzing the integrated data report of step (d) with the progression of responses to the questionnaire as obtained through sharing of user data from said subject with time and comparing them to the recommendations of the national associations; and (f) sharing the dynamic report of step (e) on the computer-readable medium with said subject for providing recommendations for lifestyle changes. In a further embodiment, the present invention provides a computer-implemented method for providing recommendations for lifestyle changes, wherein the computer-readable medium comprises open source development tools to contain information on a test for calculating biological age based on the method as disclosed herein, a virtual shopping cart for ordering said test, a scanning function for scanning a barcode of the kit of for determining the biological age of a subject as disclosed herein, a function for receiving test results from the lab, and wherein the open source development tools comprise questionnaires included in the computer-readable medium to probe lifestyle functions that impact on healthy aging, including basic physiological measures, weight, height blood pressure, heart rate, mood self-assessment, McGill pain questionnaire, diet and nutrition questionnaire, exercise questionnaire and lifestyle question including alcohol, drugs and smoking, and combination thereof.

In one embodiment, the present invention provides a computer-implemented method for providing recommendations for lifestyle changes, the method comprising the steps of: (a) assessing an entry in a computer-readable medium as obtained through sharing of user data from a subject; (b) matching the entry of step (a) to a kit for determining the biological age of a subject, comprising the means and reagents for collection and stabilizing of substrate from the subject; a scanner for reading a barcode on the kit; and instructions for collection and stabilizing of the substrate, wherein the substrate is saliva or blood of a subject, and wherein the stabilizing of substrate is for mailing in the collected substrate for extracting DNA for the measurement of DNA methylation in the extracted DNA from the substrate to obtain a DNA methylation profile of the subject to determine the biological age of said subject; (c) calculating the biological age of a subject using the method for calculating biological age of a subject as disclosed herein; (d) integrating the calculated biological age of step (c) in the machine learning model for said subject by performing statistical analysis using assessment of step (a) to obtain an integrated data report; (e) preparing a dynamic report for said subject by analyzing the integrated data report of step (d) with the progression of responses to the questionnaire as obtained through sharing of user data from said subject with time and comparing them to the recommendations of the national associations; and (f) sharing the dynamic report of step (e) on the computer-readable medium with said subject for providing recommendations for lifestyle changes, wherein the method comprises the use of Android or Apple or WeChat miniprogram for personalized lifestyle recommendations, creating a health ecosystem focused on normalizing or slowing biological aging for a subject, or for storing data in an Object storage enterprise in a server or a cloud server including, Amazon, Ali cloud or Microsoft Azure using standard data pipeline and Management systems such as Cloud dataprep across multiple subjects. In a further embodiment, the present invention provides a computer-implemented method for providing recommendations for lifestyle changes, wherein the method comprises the use of set of artificial intelligence algorithms such as Random Forest (RF), Support Vector Machine (SVM), Linear Discriminant Analysis (LDA), Generalized Linear Model (GLM) and Deep Learning (DL) for calculating the weighted contribution of different lifestyle measures on the biological age of a subject or across multiple subjects which is dynamically updated to provide personalized lifestyle recommendations on lifestyle changes.

In one embodiment, the present invention provides a computer-implemented method for providing recommendations for lifestyle changes, the method comprising the steps of: (a) assessing an entry in a computer-readable medium as obtained through sharing of user data from a subject; (b) matching the entry of step (a) to a kit for determining the biological age of a subject, comprising the means and reagents for collection and stabilizing of substrate from the subject; a scanner for reading a barcode on the kit; and instructions for collection and stabilizing of the substrate, wherein the substrate is saliva or blood of a subject, and wherein the stabilizing of substrate is for mailing in the collected substrate for extracting DNA for the measurement of DNA methylation in the extracted DNA from the substrate to obtain a DNA methylation profile of the subject to determine the biological age of said subject; (c) calculating the biological age of a subject using the method for calculating biological age across multiple subjects as disclosed herein; (d) integrating the calculated biological age of step (c) in the machine learning model for said subject by performing statistical analysis using assessment of step (a) to obtain an integrated data report; (e) preparing a dynamic report for said subject by analyzing the integrated data report of step (d) with the progression of responses to the questionnaire as obtained through sharing of user data from said subject with time and comparing them to the recommendations of the national associations; and (f) sharing the dynamic report of step (e) on the computer-readable medium with said subject for providing recommendations for lifestyle changes, wherein the method comprises the use of Android or Apple or WeChat miniprogram for personalized lifestyle recommendations, creating a health ecosystem focused on normalizing or slowing biological aging for a subject, or for storing data in an Object storage enterprise in a server or a cloud server including, Amazon, Ali cloud or Microsoft Azure using standard data pipeline and Management systems such as Cloud dataprep across multiple subjects. In a further embodiment, the present invention provides a computer-implemented method for providing recommendations for lifestyle changes, wherein the method comprises the use of set of artificial intelligence algorithms such as Random Forest (RF), Support Vector Machine (SVM), Linear Discriminant Analysis (LDA), Generalized Linear Model (GLM) and Deep Learning (DL) for calculating the weighted contribution of different lifestyle measures on the biological age of a subject or across multiple subjects which is dynamically updated to provide personalized lifestyle recommendations on lifestyle changes.

In one embodiment, the present invention provides a method for developing a computer-readable medium, the method comprising the steps of: (a) storing the data derived from multiple subjects; (b) analyzing the stored data of step (a); and (c) building a model, wherein the step of storing the data derived from multiple users comprises a cloud-based SQL data base, wherein the step of analyzing the stored data comprises a group selected from deep machine learning, reinforcement learning, and machine learning, or a combination thereof, and wherein the step of building a model comprises correlating input questionnaire measurements and the difference between DNA methylation age and chronological age as an output as well as other physiological and psychological outputs such as pain, blood pressure, BMI and mood. In a further embodiment, the present invention provides a method for developing a computer-readable medium, wherein the machine learning comprises a group selected from data mining algorithm comprising a random forest analysis or data mining algorithm comprising a K-Means Cluster Analysis or a platform comprising an Amazon Machine Learning (AML) or a software comprising H2O.ai products on platforms including Apache Hadoop Distributed File system, Amazon EC2 Google compute Engine and Microsoft Azure, or a combination thereof.

In one embodiment, the present invention provides a method for calculating biological age of a subject, the method comprising the steps of: (a) extracting DNA from a substrate from the subject; (b) measuring DNA methylation in the extracted DNA from the substrate to obtain a DNA methylation profile; (c) analyzing the DNA methylation profile to obtain a polygenic score; and (d) determining the biological age of the subject from the polygenic score, wherein the extracting DNA comprises extracting genomic DNA from saliva or blood obtained from a subject, for use in a method of assessing the effect of a biological intervention upon the biological age of a subject, the method comprising the steps of: (i) calculating the biological age of a subject using the method as disclosed herein to obtain the initial biological age before a biological intervention; (ii) performing a biological intervention upon said subject; (iii) repeating the step (i) on a subsequent substrate obtained from said subject after step (ii) has been performed to obtain the biological age after the biological intervention; (iv) integrating the biological age after the biological intervention in the machine learning model for said subject to assess the effect of the biological intervention upon the biological age of said subject, wherein the biological intervention of step (ii) is selected from a group of nutritional supplements, vitamins, therapy, administration of a test substance, dietary manipulation, metabolic manipulation, surgical manipulation, social manipulation, behavioural manipulation, environmental manipulations, sensory manipulations, hormonal manipulation and epigenetic manipulation, or combinations thereof, wherein the extracting DNA comprises extracting genomic DNA from saliva or blood obtained from a subject, and wherein the integrating the biological age after the biological intervention in the machine learning model for said subject comprises the biological age assessed in step (iii) and physiological parameters obtained through sharing of user data from said subject.

In one embodiment, the present invention provides a method for calculating biological age across multiple subjects, the method comprising the steps of: (a) extracting DNA from multiple substrates from multiple subjects; (b) measuring DNA methylation in the extracted DNA from multiple substrates to obtain a DNA methylation profile; (c) analyzing the DNA methylation profile to obtain a polygenic score; and determining the biological age across multiple subjects from the polygenic score, wherein the extracting DNA comprises extracting genomic DNA from saliva or blood obtained from a subject, for use in a method of assessing the effect of a biological intervention upon the biological age of a subject, the method comprising the steps of: (i) calculating the biological age of a subject using the method as disclosed herein to obtain the initial biological age before a biological intervention; (ii) performing a biological intervention upon said subject; (iii) repeating the step (i) on a subsequent substrate obtained from said subject after step (ii) has been performed to obtain the biological age after the biological intervention; (iv) integrating the biological age after the biological intervention in the machine learning model for said subject to assess the effect of the biological intervention upon the biological age of said subject, wherein the biological intervention of step (ii) is selected from a group of nutritional supplements, vitamins, therapy, administration of a test substance, dietary manipulation, metabolic manipulation, surgical manipulation, social manipulation, behavioural manipulation, environmental manipulations, sensory manipulations, hormonal manipulation and epigenetic manipulation, or combinations thereof, wherein the extracting DNA comprises extracting genomic DNA from saliva or blood obtained from a subject, and wherein the integrating of the biological age after the biological intervention in the machine learning model for said subject comprises the biological age assessed in step (iii) and physiological parameters obtained through sharing of user data from said subject.

In one embodiment, the present invention provides a method for calculating biological age of a subject, the method comprising the steps of: (a) extracting DNA from a substrate from the subject; (b) measuring DNA methylation in the extracted DNA from the substrate to obtain a DNA methylation profile; (c) analyzing the DNA methylation profile to obtain a polygenic score; and (d) determining the biological age of the subject from the polygenic score, wherein the extracting DNA comprises extracting genomic DNA from saliva or blood obtained from a subject, for use in a method of screening for an agent for being an anti-ageing agent, the method comprising the steps of: (i) calculating the age of a substrate obtained from a subject using the method as disclosed herein to obtain the initial biological age before a biological intervention; (ii) administering a test agent to said subject; (iii) repeating the step (i) on a subsequent substrate obtained from said subject after step (ii) has been performed to obtain the biological age after the administration of the test agent; (iv) integrating the biological age after the administration of the test agent in the machine learning model for said subject to assess whether a reduction in age has been calculated by integration in the machine learning model so to determine the test agent as an anti-ageing agent for said subject, wherein the extracting DNA comprises extracting genomic DNA from saliva or blood obtained from a subject, and wherein the integrating the biological age after the administration of the test agent in the machine learning model for said subject comprises the biological age assessed in step (iii) and physiological parameters obtained through sharing of user data from said subject.

In one embodiment, the present invention provides a method for calculating biological age across multiple subjects, the method comprising the steps of: (a) extracting DNA from multiple substrates from multiple subjects; (b) measuring DNA methylation in the extracted DNA from multiple substrates to obtain a DNA methylation profile; (c) analyzing the DNA methylation profile to obtain a polygenic score; and determining the biological age across multiple subjects from the polygenic score, wherein the extracting DNA comprises extracting genomic DNA from saliva or blood obtained from a subject, for use in a method of screening for an agent for being an anti-ageing agent, the method comprising the steps of: (i) calculating the age of a substrate obtained from a subject using the method as disclosed herein to obtain the initial biological age before a biological intervention; (ii) administering a test agent to said subject; (iii) repeating the step (i) on a subsequent substrate obtained from said subject after step (ii) has been performed to obtain the biological age after the administration of the test agent; (iv) integrating the biological age after the administration of the test agent in the machine learning model for said subject to assess whether a reduction in age has been calculated by integration in the machine learning model so to determine the test agent as an anti-ageing agent for said subject, wherein the extracting DNA comprises extracting genomic DNA from saliva or blood obtained from a subject, and wherein the integrating the biological age after the administration of the test agent in the machine learning model for said subject comprises the biological age assessed in step (iii) and physiological parameters obtained through sharing of user data from said subject.

EXAMPLES

The following examples are given by way of illustration of the present invention and therefore should not be construed to limit the scope of the present invention.

Example 1: Discovery of 13 CG Sites Contained in a DNA Region Upstream to the ElovL2 Gene, the ElovL2 AS1 Region Whose Weighted DNA Methylation Levels Predict Age in Saliva DNA In this example, the present invention relates to the "epigenetic clock", which has been recognized as the most accurate measure of biological age to date. However, the tests that have been available to date require measuring DNA methylation at many sites (~350) using blood which is an invasive and costly method which is not applicable to as a widely distributed consumer product. Although available methods are adequate for research and clinical related research, they are not feasible for consumer driven public-wide use of this test. Thus, the present invention provides a method that is an accurate, robust, high throughput and noninvasive test of biological aging based on the "epigenetic clock", particularly DNA methylation. The present invention in this example provides polyCG DNA methylation markers of biological age for lifestyle management of healthy aging.

Discovery of CG Sites that Correlate with Age in Blood

Figure 2:
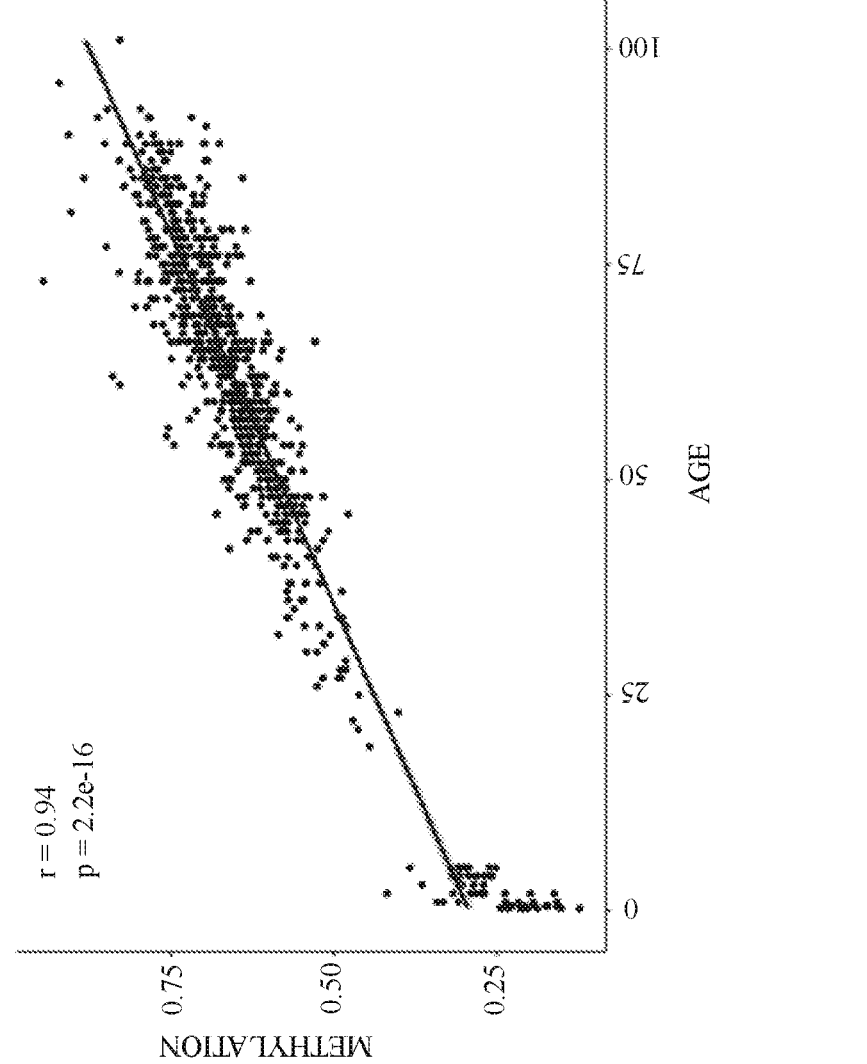
FIG. 2. ElovL2 AS1 region CG sites are highly correlated with age in saliva. The correlation between methylation score of weighted methylation levels of CG sites in ElovL2 AS1 region, namely, cg16867657, cg21572722 as positioned in chromosome 6 and cg09809672 as positioned in chromosome 1 (refer to Table 1 positions in genome) and age in publicly available blood Illumina 450K arrays (GSE40279 n=656 and GSE2219, n=60) is depicted. The analysis reveals a strong correlation between methylation and age across all ages.

The present invention subjected the publicly available 450K Illumina genome wide DNA methylation arrays from blood (GSE40729) to Pearson correlation analysis. A smaller number of CG sites were selected and analyzed which have not been previously reported. Two of those CG sites were found to be upstream of the antisense region of the ElovL2 gene referred to as the ElovL2 AS1 region as depicted in the form of a representative example in FIG. 1 as disclosed herein for physical map, where, as shown therein, they were found to be highly correlated with age (with a Pearson correlation coefficient r>0.9 and p=0). The present invention then determined that a combined weighted DNA methylation measurement for both of the said CG sites predicted age accurately in blood DNA in an independent cohort (GSE40279 n=656 and GSE2219, n=60) as depicted in FIG. 2, as disclosed herein. It was seen that the methylation of the CG sites in the ElovL2 AS1 region as set forth in SEQ ID NO:1 as disclosed herein, progressed from close to 0% in fetuses to close to 90% in 90-year-old people. Thus, this ElovL2 AS1 region as set forth in SEQ ID NO:1 and the CG sites found within the said region and are the positions of the di-nucleotide sequence as described in Table 1 as disclosed herein, single-handedly showed almost a perfect correlation with age suggesting that a small number of the said CG sites might be sufficient for determining the biological age.

The CG Sites in the ElovL2 AS1 Region Predict Age in Saliva Samples

Figure 3:
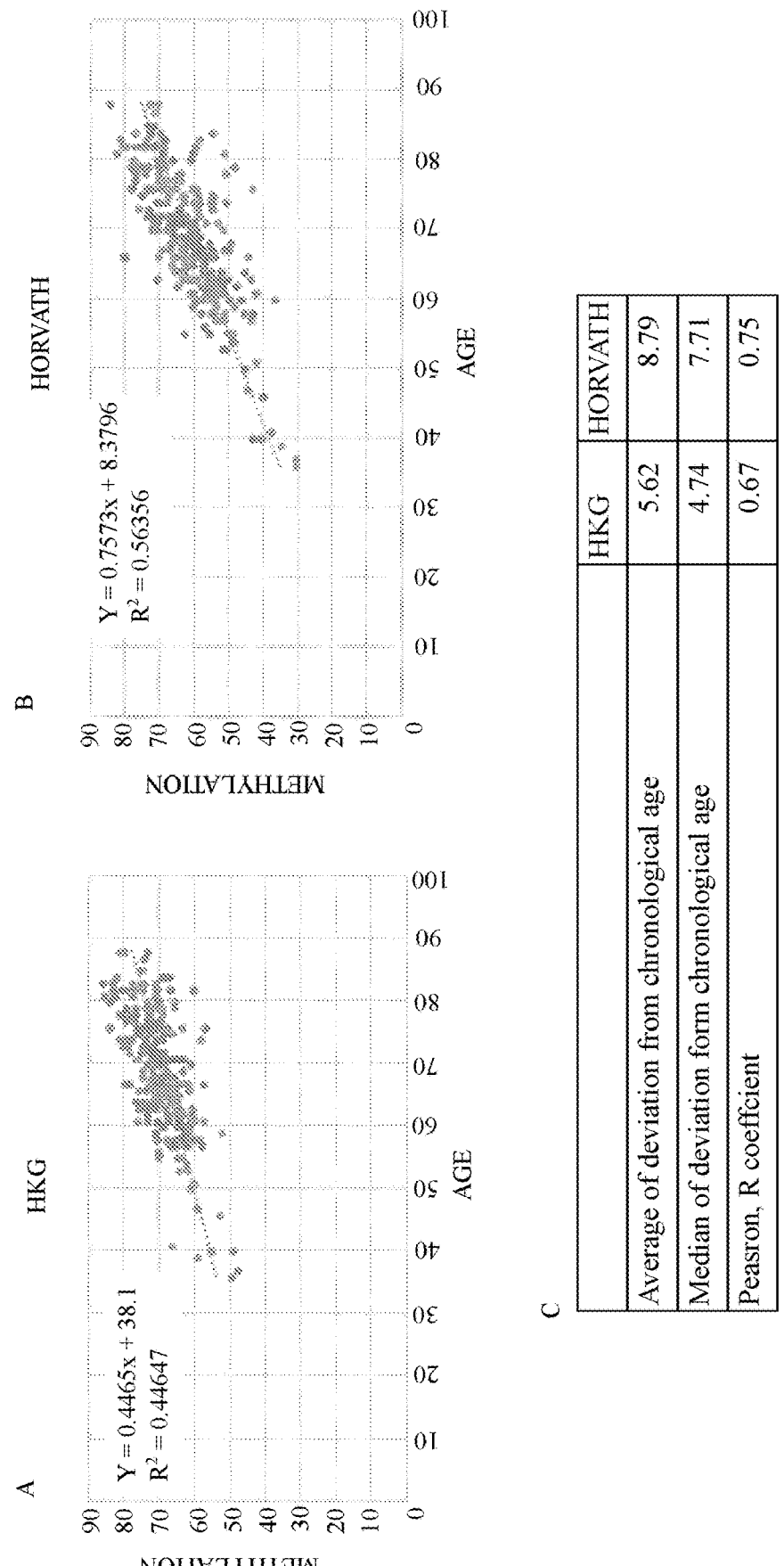
FIG. 3. Correlation of methylation at ElovL2 AS1 region CG sites and age in saliva, and comparison with Horvath epigenetic clock. The correlation of methylation at ElovL2 AS1 region CG sites, namely, cg1687657 and cg21572722 and age in saliva and its comparison with Horvath epigenetic clock is depicted. A. Correlation between combined methylation score of cg1687657 and cg21572722 (HKG) and age using DNA methylation profiles from saliva from GSE78874. B. Correlation between the gold standard Horvath methylation clock score using the same Illumina 450K data. C. Comparison of the accuracy of the two tests. The combined score of these two sites have a lower average deviation in prediction age than the Gold standard Horvath clock.

To assess the wide applicability of the disclosed DNA methylation age tests it is important that they do not require qualified health professionals for deriving the biological material. In this example, the present invention determined whether it was possible to use the disclosed highly correlated CG sites, which are the positions of the di-nucleotide sequence as described in Table 1 located in the ElovL2 AS1 region as set forth in SEQ ID NO:1 disclosed herein, as age predictors in saliva by testing publicly available 450K Illumina arrays methylation data for saliva (GSE78874, n=259). The present invention disclosed a methylation score composed of the weighted methylation measurements for cg16867657, and cg21572722, which are the positions of the di-nucleotide sequence as described in Table 1 and are positions of the CG sites in the region as set forth in SEQ ID NO:1, the ElovL2 AS1 region along with cg09809672, which is a CG site in chromosome 1 as described in Table 1 as disclosed herein that predicted age with an average deviation of 5.62 years and median deviation of 4.74 years. The present invention then compared the accuracy of the disclosed model herein with the gold standard, Horvath clock. As seen in FIG. 3, the performance of the ElovL2 AS1 region sites was slightly better than the Horvath clock. It is to be noted that the value of the ElovL2 gene in age detection is known in the art. The present invention however discloses that the said past knowledge has missed the fact that the two CG sites (namely, cg16867657 and cg21572722) that were thought to be residing in the ElovL2 gene are really upstream to a different gene in the antisense orientation to the ElovL2 gene the ElovL2-AS1 gene (refer to physical description depicted in FIG. 1 as disclosed herein), where the said upstream region is referred to as the ElovL2 AS1 region and disclosed herein as set forth in SEQ ID NO:1. This region upstream of the ElovL2-AS1 gene contains the selected 13 CG sites (refer to Table 1 as disclosed herein above).

Example 2: Bisulfite Conversion, Multiplex Amplification and Next Generation Sequencing and Calculation of Methylation for 13 CGs in the ElovL2 AS1 Region The present disclosure further provides that the saliva to be collected by a subject or a customer in the DNA stabilization buffer (Tris 10 mM EDTA 10 mM, SDS 1%) to be mailed by them to the lab, was incubated with protease K (200 microgram for 30 minutes at 37° C.) at the lab. Then the genomic DNA was purified using a Qiagen kit. The purified DNA was treated with sodium bisulfite using for example, the EZ DNA bisulfite treatment kit. A library of targeted sequences was generated by two-step PCR reactions using the following primers in a standard Taq polymerase reaction:

For PCR 1—amplifying the amplicon corresponding to the sequence as set forth in SEQ ID NO:1:

```
Forward primer as set forth in SEQ ID NO: 5:
5'ACACTCTTTCCCTACACGACGCTCTTCCGATCNNNNNNNYGGGYGGYGA

TTTGTAGGTTTAGT3'

Reverse primer as set forth in SEQ ID NO: 6:
5'GTGACTGGAGTTCAGACGTGTGCTCTTCCGATCTCCCTACACRATAC

TACTTCTCCCC3'
```

For PCR 2—to barcode the samples, a second PCR reaction was performed with the following primers:

```
Forward primer as set forth in SEQ ID NO: 7:
5'AATgATACggCgACCACCgAgATCTACACTCTTTCCCTACACgAC3'

Barcoding (reverse) primer as set forth in SEQ ID
NO: 8:
5'CAAGCAGAAGACGGCATACGAGATAGTCATCGgTGACTGGAGTTCA GACGTG3'
(red bases are the index; up to 200 variations of
this index is used).
```

The second set of primers introduced the index for each sample as well as the reverse and forward sequencing primers. The PCR product 2 from all samples were combined and purified on AMPpure-XP beads (NEB). The library was quantified by QPCR and loaded onto a MiSeq flow cell. The fast Q file were aligned with the relevant genomic region using BisMark or other editing software.

Example 3: Superior Performance of 13 CG Sites in the Region Upstream of ElovL2-AS1 Gene Region, the ElovL2 AS1 Region as Set Forth in SEQ ID NO:1

Figure 4:
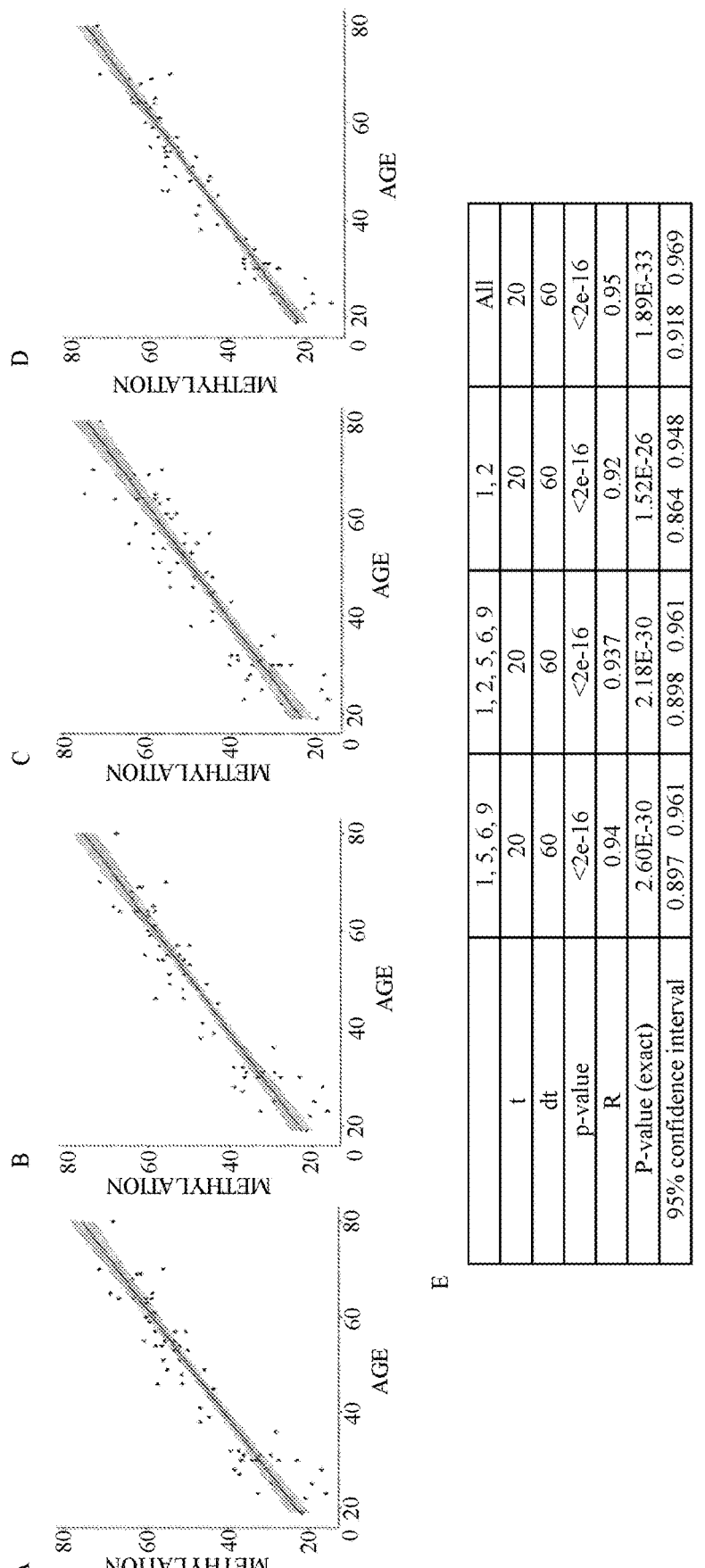
FIG. 4. Prediction of age using the 13 CG ElovL2 AS1 polygenic score in saliva. The utility of the present invention is depicted. A. Methylation scores predicting age calculated with a linear regression equation predicting age as a function of the weighted methylation levels of CG sites 1, 5, 6, 9 in ElovL2 AS1 region (refer to Table 1 for positions in genome) using methylation levels from 65 people saliva DNA. The ElovL2 AS1 region as described in FIG. 1 was amplified from bisulfite converted saliva DNA and subjected to multiplexed-next generation sequencing on a Miseq next generation sequencer. B. Methylation scores predicting age calculated with a linear regression equation predicting age as a function of the weighted methylation levels of CG sites 1, 2, 5, 6, 9 in ElovL2 AS1 region (refer to Table 1 for positions in genome). C. Methylation scores predicting age calculated with a linear regression equation predicting age as a function of the weighted methylation levels of CG sites 1, 2 in ElovL2 AS1 region (refer to Table 1 for positions in genome). D. Methylation scores predicting age calculated with a linear regression equation predicting age as a function of the weighted methylation levels of all CG sites in ElovL2 AS1 region (refer to Table 1 for positions in genome). E. Comparison of the predictive value of the different methylation scores. An equation that includes all 13 CG sites is superior to any other combination.

Next, the present disclosure determined whether a combined weighted methylation score of the disclosed 13 CG sites provided a superior predictive performance when compared to either 2 or 3 CG sites. Saliva samples were collected from 65 volunteers in Hong Kong Science park and the methylation levels at 13 CG sites (refer to Table 1 as disclosed herein above) was determined as described in Example 2. The present disclosure performed a series of polyvariable linear regressions with different combinations of CG sites. The results as shown in FIG. 4 as disclosed herein, illustrated that a combination of 13 CG sites (refer to part D of FIG. 4) performed better than a combination of either 4 CG sites (refer to part A of FIG. 4), 5 CGs (refer to part B of FIG. 4) or the Illumina 2 CG sites (refer to part C of FIG. 4). The result with respect to the superiority of the combination of 13 CG sites over smaller combinations of 4, 5 or 2 CG sites was further demonstrated with the statistical comparison data as shown in FIG. 4E. The Pearson product-moment correlation coefficient r for 13 CG methylation score was 0.95 (p=1.8×10−33).

Example 4: Determining Biological Age in Saliva Samples from Customers

Biological age is an important parameter of our health as discussed herein above. However, since the test as disclosed in the present invention is meant to be taken by subjects, who are customers at their homes outside the professional health care system, it is important that the test is simple, does not require a health professional to draw blood as a preferred embodiment since, blood collection in itself may be a mildly risky procedure and that it could be delivered to a central state of the art lab facility by regular surface mail. Thus, the present invention discloses that the 13 CG sites in the ElovL2 AS1 region forms the basis of the EpiAging test that provides such an opportunity. In the present invention as disclosed, the customer orders a saliva test kit that contains a stabilization buffer that keeps DNA stable for up to 1 month through the EpiAging App, web or e-mail. The stabilization buffer contains 20 mM Tris-HCl (pH 8.0), 20 mM EDTA, 0.5% SDS and 1% Triton X-100. The bar-coded kit arrives by mail at his residence. The customer scans the bar code with his scanner on his phone and registers his barcode in the App which links the barcode to his phone internal ID. Following the instructions provided in the EpiAging test kit, the customer spits to the collection tube and then transfers the saliva to the tube containing the stabilization buffer and places the tube in a prepaid postage envelop and sends it to the lab. In the lab, DNA is extracted, bisulfite converted (the chemical bisulfite conversion treatment converts unmethylated C to T while methylated C remain as C) and ElovL2 AS1 region is amplified as described in Example 3 and sequenced with samples from other patients on a MiSeq Illumina sequencer. The fastQ files are analyzed and methylation values (m) for the 13 CG sites are calculated mCGn=CGnC counts/(CGnT counts+ CGnC counts).

The values are then entered into the following equation to calculate the biological age:

$$\begin{aligned} \text{Biological age} = (&CG1*87.5643 + CG2*6.3301 + CG3*-\\ &0.8691 + CG4*1.9468 + CG5*40.0336 +\\ &CG6*49.4303 + CG7*-14.7868 + CG8*22.9042 +\\ &CG9*-49.7942 + CG10*111.7467 +\\ &CG11*41.8108 + CG12*0.4144 + CG13*-\\ &150.8005) - 71.6872 \end{aligned}$$

The biological age is then sent to the customer on his EpiAging App or the customer can retrieve the results using his barcode ID. A significantly older biological age than chronological age (+5 y) serves as a "red flag" for lifestyle changes. The customer measures his biological age periodically (every 6-12 months) and assesses progress in reducing gap between biological and chronological age.

Example 5: EpiAging App for Management of Biological Age Testing and Lifestyle Data The present invention discloses an EpiAging App which conforms to either Apple and Android operating systems and provides information about the "EpiAging test", how to order, a cart for ordering and link to e-payment such as PayPal or Alipay. The innovative aspect of the disclosed App of the present invention is that it combines the customer based management of the "EpiAging test" with a system for customer driven management of lifestyle changes based on dynamic recommendations by reputable national and international medical groups, "self-reporting", sharing data, machine learning, iterative changes driven by iterative machine learning, personalized reports to customers and repeated assessments. The system of "reinforced learning" instructs lifestyle changes that have the greatest impact on reducing aging acceleration as determined by the difference between DNA methylation age and chronological age. The App provided herein is built by programs that are open source and known to anyone skilled in the art such as Build Fire JS, Ionic, Appcelerator's Titanium SDK, Mobile angular UI, and Siberian CMS.

The App is downloaded either from Apple store, Google play store and Web sites. The App requires registration and assignment of customer ID. The App activates a scanner which scans the bar code and links the test barcode and the customer's ID. Data will be linked to these "blinded" IDs. Personal data and customer data are separated "fire walled" and tokenized to secure complete blinding of the "aging" and lifestyle data. The data management system has no access to the personal data. A system is built to restore personal IDs which can be initiated only by the customer using his email account but completely blinded from the data management system. Blinding of data is a fundamental feature of the App.

The front page of the app contains several buttons. One button links to basic information about the "aging"-test and scientific citations and PubMed links for further and deeper knowledge of the area.

The info provides information on the link between lifestyle and "aging". A second button links to a page which contains a series of buttons that link to life style and well-being domains buttons such as "mood", "chronic pain", "nutrition" including intake of nutritional supplements such as SAMe, Vitamins etc., "physiological measures" such as blood pressure, heart rate, weight, height, fasting sugar levels and other metabolic tests, medications, drugs of abuse, alcohol, smoking and exercise data entered by the customer. Each section is preceded by recommendations which are collated from reputable associations such as the National Heart and Stroke associations or Diabetes associations, American Cancer Society etc. The recommendations section contains a link to these associations so that customer Could make his own judgements and decisions. The idea behind the lifestyle management section is self-empowerment and customer's control of his/her lifestyle decisions. The data entry is done by moving a scale that is numerical. Yes-No entries are scaled as 0 for NO and 1 for yes. Other quantifiable entries are entered as by their quantity. On top of each data entry scale, a scaled presentation of the recommendation is presented providing the customer with an estimate of his performance relative to recommendations which is color coded. The recommended range is indicated by green color. Deviation from recommendations is indicated by red above and blue below range. A save button which is clicked by the customer upon conclusion of each section data entry enables saving of the data. A summary analysis report is provided once data is entered. Charts that describe the progress over time in relation to the national recommendation is provided as well. Once lab aging test is completed the tests are delivered remotely to the App. The customer data as well as other customer's data are stored in the cloud-based data base for further analysis.

Example 6: Machine Learning Driven Analysis of Health and DNA Methylation Age Data and Personalized Recommendation for Lifestyle Improvements The data derived from multiple users is stored in a cloud-based SQL data base. "Machine learning" algorithms are used for analysis of the data and are building models correlating input questionnaire measurements such as pain, blood pressure, BMI and mood and the difference between DNA methylation age and chronological age as an output. For example, using methods such as "neural networks", Decision Trees, Random Forests Lasso regression, K-Means Cluster analysis, Reinforcement Learning and "penalized regression".

The method as disclosed in the present invention comprises performing statistical analysis on the response to the questionnaires and providing a dynamic report to the consumers on the App that describes the progression of responses to the questionnaire with time as compared to recommendations of the national associations such as Cancer, heart and Stroke and diabetes.

Although the invention has been explained in relation to its preferred embodiment, it is to be understood that many other possible modifications and variations can be made without departing from the spirit and scope of the invention.

ADVANTAGES

The innovative aspect of the method as disclosed in the present invention over what is known in the art is that the combination of 13 CG sites in the previously undescribed ElovL2 AS1 region provides an extremely highly accurate prediction of age from saliva samples in one single amplicon. Accuracy and simplicity are enhanced by multiplexing and use of robust next generation sequencing. This approach dramatically reduces cost and renders the test feasible for application as a consumer product.

REFERENCES

Beauchaine, T. P., & Beauchaine, R. J., 3rd. (2002). A comparison of maximum covariance and K-means cluster analysis in classifying cases into known taxon groups. *Psychol Methods*, 7(2), 245-261.

Bybee, S. M., Bracken-Grissom, H., Haynes, B. D., Hermansen, R. A., Byers, R. L., Clement, M. J., . . . Crandall, K. A. (2011). Targeted amplicon sequencing (TAS): a scalable next-gen approach to multilocus, multitaxa phylogenetics. *Genome Biol Evol*, 3, 1312-1323. doi:10.1093/gbe/evr106

Chen, B. H., Marioni, R. E., Colicino, E., Peters, M. J., Ward-Caviness, C. K., Tsai, P. C., . . . Horvath, S. (2016). DNA methylation-based measures of biological age: meta-analysis predicting time to death. *Aging* (Albany N.Y.), 8(9), 1844-1865. doi:10.18632/aging.101020

Colella, S., Shen, L., Baggerly, K. A., Issa, J. P., & Krahe, R. (2003). Sensitive and quantitative universal Pyrosequencing methylation analysis of CpG sites. *Biotechniques*, 35(1), 146-150.

De Roach, J. N. (1989). Neural networks—an artificial intelligence approach to the analysis of clinical data. *Australas Phys Eng Sci Med*, 12(2), 100-106.

Ferrucci, L., Cavazzini, C., Corsi, A., Bartali, B., Russo, C. R., Lauretani, F., . . . Guralnik, J. M. (2002). Biomarkers of frailty in older persons. *J Endocrinol Invest*, 25(10 Suppl), 10-15.

Freire-Aradas, A., Phillips, C., Mosquera-Miguel, A., Giron-Santamaria, L., Gomez-Tato, A., Casares de Cal, M., . . . Lareu, M. V. (2016). Development of a methylation marker set for forensic age estimation using analysis of public methylation data and the Agena Bioscience EpiTYPER system. *Forensic Sci Int Genet*, 24, 65-74. doi:10.1016/j.fsigen.2016.06.005

Hardy, A., & Magnello, M. E. (2002). Statistical methods in epidemiology: Karl Pearson, Ronald Ross, Major Greenwood and Austin Bradford Hill, 1900-1945. *Soz Praventivmed*, 47(2), 80-89.

Hertel, J., Friedrich, N., Wittfeld, K., Pietzner, M., Budde, K., Van der Auwera, S., . . . Grabe, H. J. (2016). Measuring Biological Age via Metabonomics: The Metabolic Age Score. *J Proteome Res,* 15(2), 400-410. doi: 10.1021/acs.jproteome.5b00561

Horvath, S. (2013). DNA methylation age of human tissues and cell types. *Genome Biol,* 14(10), R115. doi:10.1186/gb-2013-14-10-r115

Jylhävä, J., Pedersen, N. L., & Hagg, S. (2017). Biological Age Predictors. *EBioMedicine,* 21, 29-36. doi:10.1016/j.ebiom.2017.03.046

Kakushadze, Z., & Yu, W. (2017). *K-means and cluster models for cancer signatures. *Biomol Detect Quantif,* 13, 7-31. doi:10.1016/j.bdq.2017.07.001

Kim, S. M., Kim, Y., Jeong, K., Jeong, H., & Kim, J. (2018). Logistic LASSO regression for the diagnosis of breast cancer using clinical demographic data and the BI-RADS lexicon for ultrasonography. *Ultrasonography,* 37(1), 36-42. doi:10.14366/usg.16045

Kristensen, L. S., Mikeska, T., Krypuy, M., & Dobrovic, A. (2008). Sensitive Melting Analysis after Real Time-Methylation Specific PCR (SMART-MSP): high-throughput and probe-free quantitative DNA methylation detection. *Nucleic Acids Res.*

Mann, J. J., Ellis, S. P., Waternaux, C. M., Liu, X., Oquendo, M. A., Malone, K. M., . . . Currier, D. (2008). Classification trees distinguish suicide attempters in major psychiatric disorders: a model of clinical decision making. *J Clin Psychiatry,* 69(1), 23-31.

Marioni, R. E., Harris, S. E., Shah, S., McRae, A. F., von Zglinicki, T., Martin-Ruiz, C., . . . Deary, I. J. (2018). The epigenetic clock and telomere length are independently associated with chronological age and mortality. *Int J Epidemiol,* 47(1), 356. doi:10.1093/ije/dyx233

Monaghan, P. (2010). Telomeres and life histories: the long and the short of it. *Ann N Y Acad Sci,* 1206, 130-142. doi:10.1111/j.1749-6632.2010.05705.x Mupparapu, M., Wu, C. W., & Chen, Y. C. (2018). Artificial intelligence, machine learning, neural networks, and deep learning: Futuristic concepts for new dental diagnosis. *Quintessence Int,* 49(9), 687-688. doi:10.3290/j.qi.a41107

Sherbet, G. V., Woo, W. L., & Dlay, S. (2018). Application of Artificial Intelligence-based Technology in Cancer Management: A Commentary on the Deployment of Artificial Neural Networks. *Anticancer Res,* 38(12), 6607-6613. doi:10.21873/anticanres.13027

Shi, T., Seligson, D., Belldegrun, A. S., Palotie, A., & Horvath, S. (2005). Tumor classification by tissue microarray profiling: random forest clustering applied to renal cell carcinoma. *Mod Pathol,* 18(4), 547-557. doi:10.1038/modpathol.3800322

Svetnik, V., Liaw, A., Tong, C., Culberson, J. C., Sheridan, R. P., & Feuston, B. P. (2003). Random forest: a classification and regression tool for compound classification and QSAR modeling. *J Chem Inf Comput Sci,* 43(6), 1947-1958. doi:10.1021/ci034160g Vetter, V. M., Meyer, A., Karbasiyan, M., Steinhagen-Thiessen, E., Hopfenmuller, W., & Demuth, I. (2018). Epigenetic clock and relative telomere length represent largely different aspects of aging in the Berlin Aging Study II (BASE-II). *J Gerontol A Biol Sci Med Sci.* doi:10.1093/gerona/gly184

Yanai, H., Budovsky, A., Tacutu, R., & Fraifeld, V. E. (2011). Is rate of skin wound healing associated with aging or longevity phenotype? *Biogerontology,* 12(6), 591-597. doi:10.1007/s10522-011-9343-6

Yu, M., Heinzerling, T. J., & Grady, W. M. (2018). DNA Methylation Analysis Using Droplet Digital PCR. *Methods Mol Biol,* 1768, 363-383. doi:10.1007/978-1-4939-7778-9_21

Zhao, Y., Kosorok, M. R., & Zeng, D. (2009). Reinforcement learning design for cancer clinical trials. *Stat Med,* 28(26), 3294-3315. doi:10.1002/sim.3720

What is claimed is:

1. A method for calculating biological age of a subject, the method comprising the steps of:
    (a) extracting DNA from a saliva sample obtained from the subject;
    (b) measuring DNA methylation in the extracted DNA from the saliva sample to obtain a DNA methylation profile;
    (c) analyzing the DNA methylation profile to obtain a polygenic score; and
    (d) determining the biological age of the subject from the polygenic score,
wherein the measuring DNA methylation consists of measuring the methylation status of each CG site of a set of CG sites of the ElovL2 AS1 region as set forth in SEQ ID NO: 1, the set of CG sites consisting of the CG sites positioned at genomic coordinates 56-57, 59-60, 62-63, 68-69, 70-71, 72-73, 75-76, 83-84, 89-90, 111-112, 123-124, 130-131 and 138-139 in the sequence as set forth in SEQ ID NO: 1;
wherein the measuring DNA methylation is performed using targeted-amplicon next generation bisulfite sequencing, which comprises amplifying genomic DNA extracted from the saliva sample with target specific primers as set forth in SEQ ID NO:5 for the forward primer and SEQ ID NO:6 for the reverse primer to obtain PCR product 1, amplifying the PCR product 1 with barcoding primers to obtain PCR product 2, performing multiplexed next generation bisulfite sequencing in a single reaction using the PCR product 2, extracting data from the multiplexed sequencing step, and quantifying DNA methylation from the extracted data to obtain the DNA methylation profile;
or using DNA pyrosequencing comprising primers as set forth in SEQ ID NO:2 for a forward, biotinylated primer, SEQ ID NO:3 for a reverse primer, and SEQ ID NO:4 for a pyrosequencing primer.

2. The method of claim 1, wherein the analyzing the DNA methylation profile to obtain a polygenic score comprises using multiple linear regression equations or neural network analysis.

3. The method of claim 1, further comprising performing the method of claim 1 on multiple subjects.

4. The method of claim 3, wherein the measuring the methylation status of each CG site of the set of CG sites of the ElovL2 AS1 region comprises
    (a) amplifying genomic DNA extracted from multiple saliva samples with target specific primers to obtain PCR product 1;
    (b) amplifying the PCR product 1 of step (a) with barcoding primers to obtain PCR product 2;
    (c) performing multiplexed next generation bisulfite sequencing in a single reaction using the PCR product 2 of step (b);
    (d) extracting data from the multiplexed sequencing of step (c); and
    (e) quantifying DNA methylation from the extracted data of step (d) to obtain a DNA methylation profile for each saliva samples, wherein the target specific primers to obtain PCR product 1 comprise primers as set forth in SEQ ID NO:5 for the forward primer and SEQ ID NO:6 for the reverse primer, and wherein the primers to obtain PCR product 2 comprise primers as set forth in SEQ ID NO:7 for the forward primer and SEQ ID NO:8 for the reverse primer.

5. The method of claim 1 for use in a method of assessing the effect of a biological intervention upon the biological age of a subject, the method comprising the steps of:
    (a) determining the biological age of a subject using the method of claim 1 to obtain the initial biological age before a biological intervention;
    (b) performing a biological intervention upon said subject;
    (c) repeating the step (a) on a subsequent saliva sample obtained from said subject after step (b) has been performed to obtain the biological age after the biological intervention;
    (d) integrating the biological age after the biological intervention in a machine learning model for said subject to assess the effect of the biological intervention upon the biological age of said subject,
    wherein the biological intervention of step (b) is selected from the group consisting of nutritional supplements, vitamins, therapy, administration of a test substance, dietary manipulation, metabolic manipulation, surgical manipulation, social manipulation, behavioural manipulation, environmental manipulations, sensory manipulations, hormonal manipulation and epigenetic manipulation, and combinations thereof, and
    wherein the integrating the biological age after the biological intervention in the machine learning model for said subject comprises the biological age assessed in step (c) and physiological parameters obtained through sharing of user data from said subject.

6. The method of claim 1 for use in a method of screening for an agent for being an anti-ageing agent, the method comprising the steps of:
    (a) determining the biological age of a subject using the method of claim 1 to obtain the initial biological age before administration of a test agent;
    (b) administering the test agent to said subject;
    (c) repeating the step (a) on a subsequent saliva sample obtained from said subject after step (b) has been performed to obtain the biological age after the administration of the test agent;
    (d) integrating the biological age after the administration of the test agent in a machine learning model for said subject to assess whether a reduction in age has been calculated to determine if the test agent is an anti-ageing agent for said subject, and
    wherein the integrating the biological age after the administration of the test agent in the machine learning model for said subject comprises the biological age assessed in step (c) and physiological parameters obtained through sharing of user data from said subject.

* * * * *